United States Patent
Eling et al.

(10) Patent No.: US 7,141,661 B2
(45) Date of Patent: Nov. 28, 2006

(54) NON-STEROIDAL ANTI-INFLAMMATORY DRUG ACTIVATED GENE WITH ANTI-TUMORIGENIC PROPERTIES

(75) Inventors: Thomas E. Eling, Raleigh, NC (US); Seung Joon Baek, Knoxville, TN (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 200 days.

(21) Appl. No.: 10/363,514

(22) PCT Filed: Sep. 6, 2001

(86) PCT No.: PCT/US01/27544

§ 371 (c)(1),
(2), (4) Date: Aug. 15, 2003

(87) PCT Pub. No.: WO02/20759

PCT Pub. Date: Mar. 14, 2002

(65) Prior Publication Data

US 2004/0029770 A1 Feb. 12, 2004

Related U.S. Application Data

(60) Provisional application No. 60/231,246, filed on Sep. 8, 2000.

(51) Int. Cl.
*C07H 21/04* (2006.01)
*C12N 15/09* (2006.01)
*C12Q 1/68* (2006.01)
*A01K 67/027* (2006.01)

(52) U.S. Cl. .............. 536/23.2; 536/23.5; 536/24.1; 435/320.1; 435/6

(58) Field of Classification Search .................. None
See application file for complete search history.

(56) References Cited

FOREIGN PATENT DOCUMENTS

| EP | 0 629 697 A2 | 12/1994 |
|---|---|---|
| WO | WO 97/00958 A1 | 1/1997 |
| WO | WO 98/11224 A1 | 3/1998 |

OTHER PUBLICATIONS

Lawton et al., Gene, 203:17-26, 1997.*
Nierman WC and Maglott DR. 1994. ATCC/NIH Repository Catalog of human and Mouse DNA Probes and libraries, 8th edition. Rockville, MD. p. 155.*
Bootcov MR et al. 1997. MIC-1, a novel macrophage inhibitory cytokine, is a divergent member of the TGF-beta superfamily. Proc Natl Acad Sci U S A. 94(21):11514-9.*
Baek et al., *Molecular Pharmacology*, 59(4), 901-908 (2001).
Baek et al., *Journal of Biological Chemistry*, 276(36), 33384-33392 (2001).
Lawton et al., *Gene*, 203(1), 17-26 (1997).

* cited by examiner

*Primary Examiner*—Daniel M. Sullivan
*Assistant Examiner*—Laura McGillem
(74) *Attorney, Agent, or Firm*—Leydig, Voit & Mayer, Ltd.

(57) ABSTRACT

The present invention provides methods and compositions for drug screens to identify and characterize agents that are agonistic or antagonistic to activation of the promoter region of the NAG-1 gene. Activation of the NAG-1 gene is associated with the apoptotic elimination of cancer cells both in vitro and in vivo. The invention also provides novel promoter region sequences of the NAG-1 gene.

8 Claims, 14 Drawing Sheets

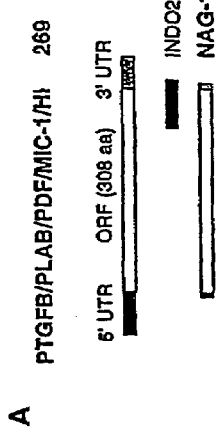
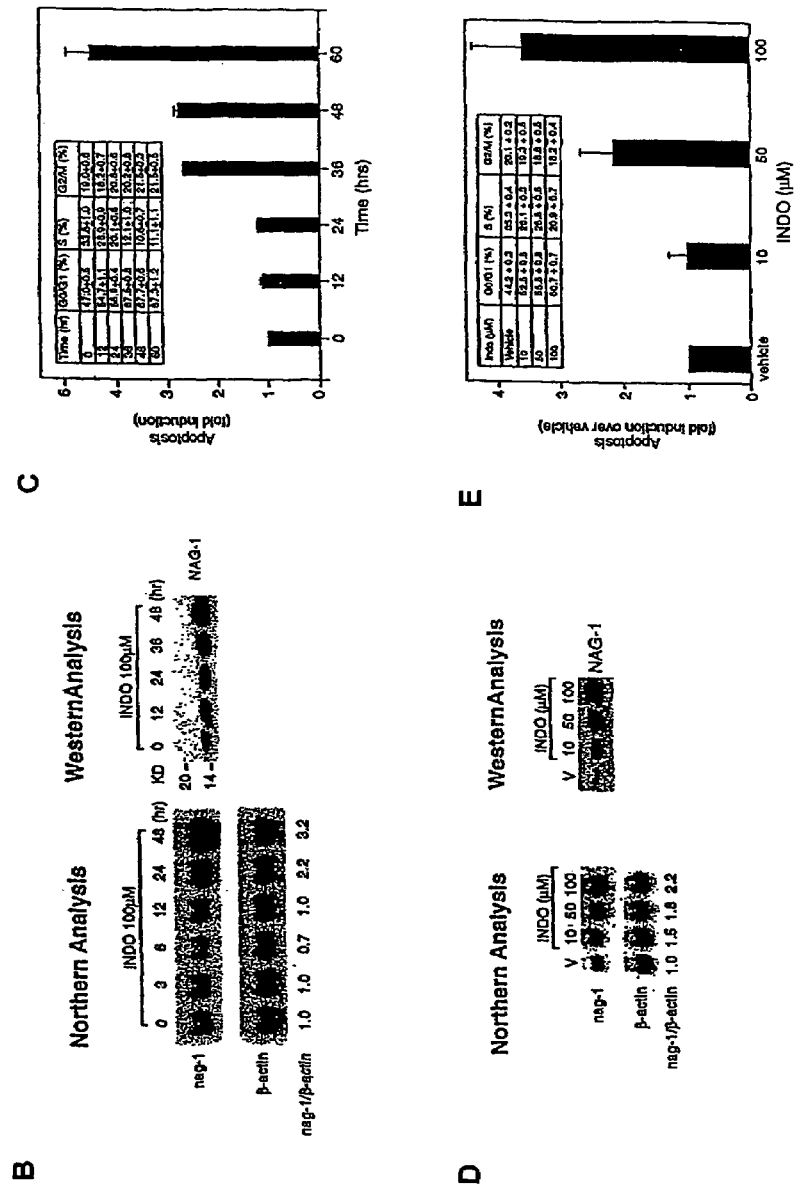
Figure 1

Figure 2
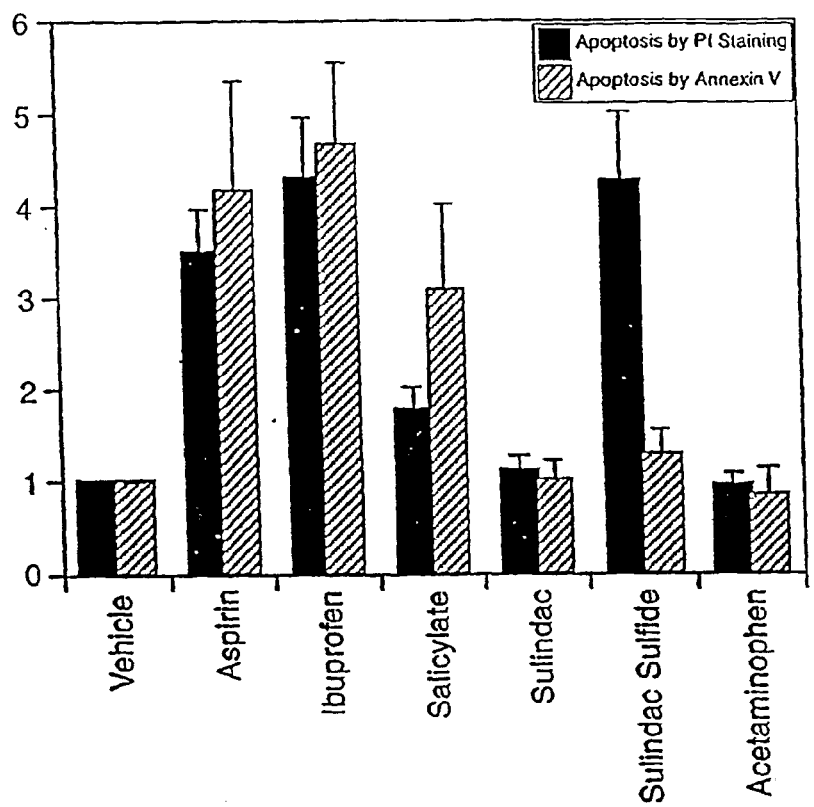
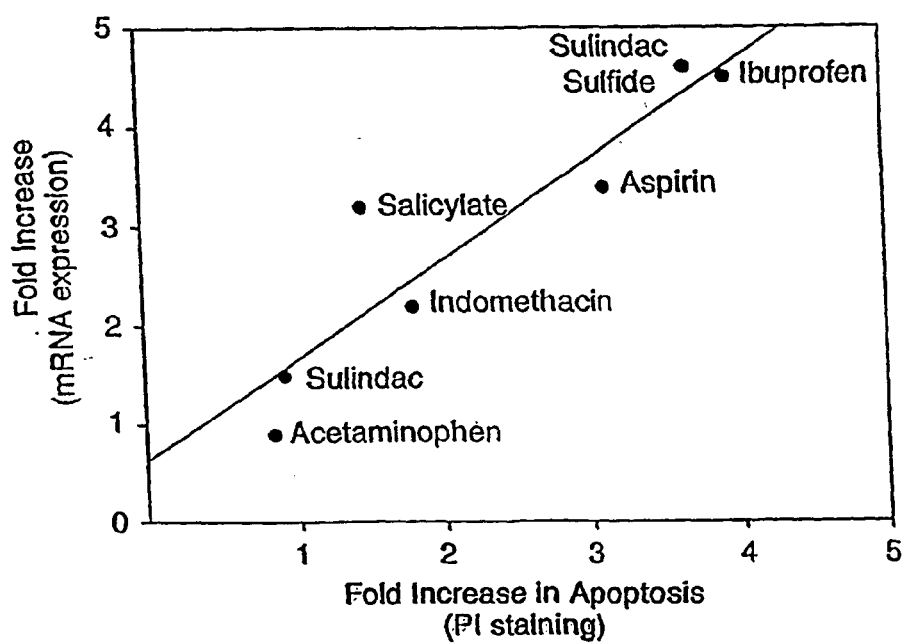

Figure 4
A
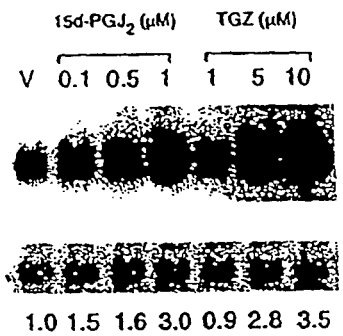
B
Northern Analysis
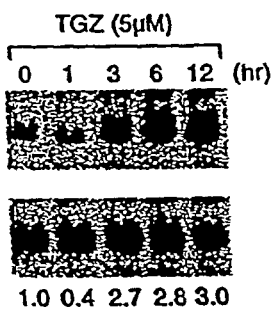
WesternAnalysis
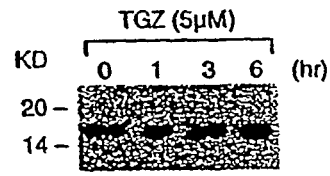
C
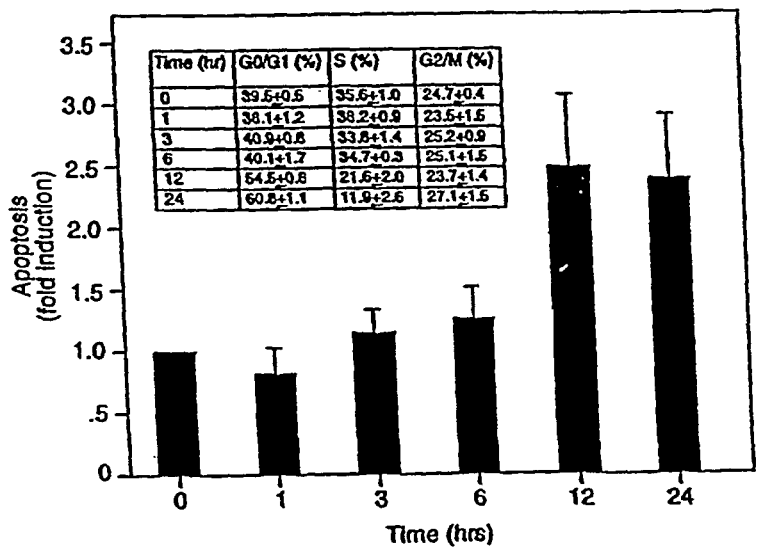

Figure 5
A
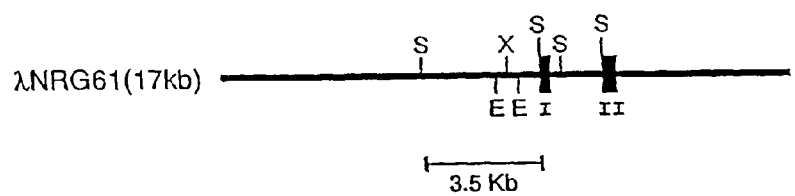
B
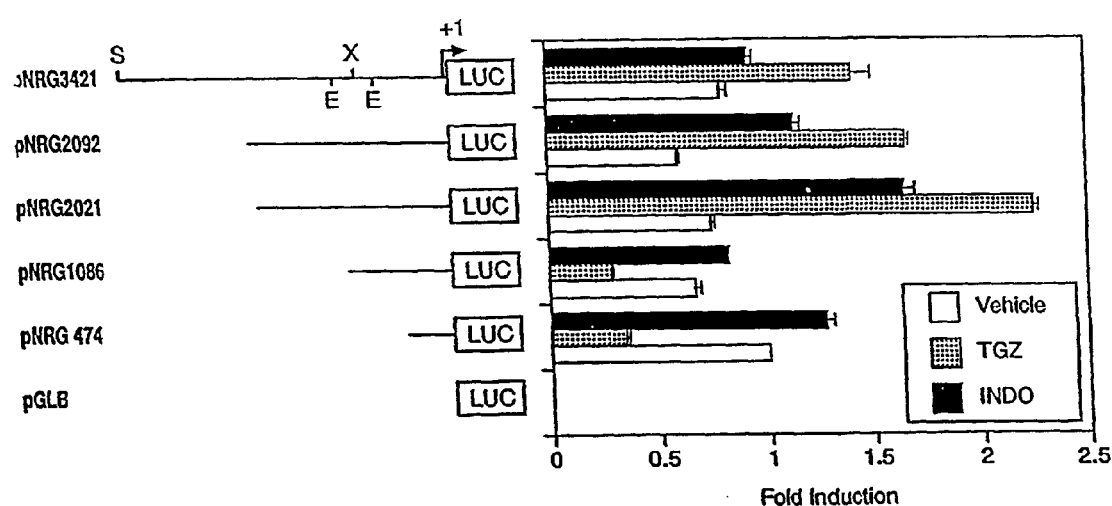
C
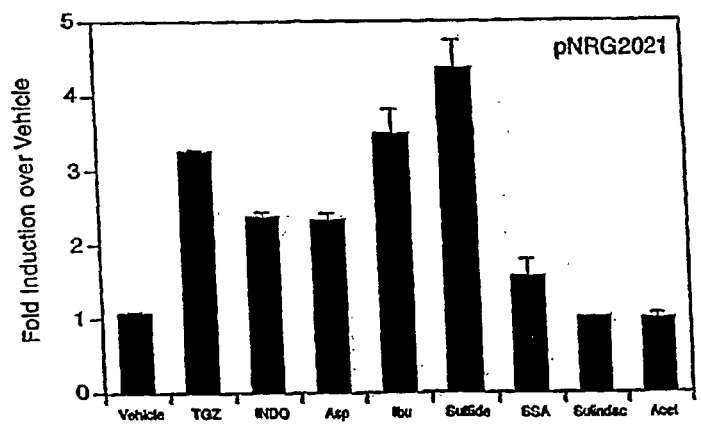

Figure 6
A
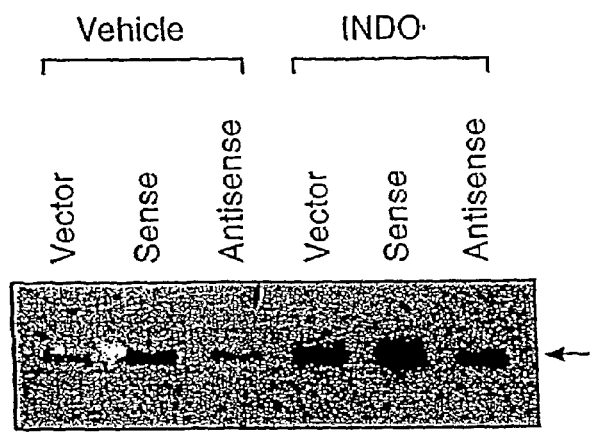
B
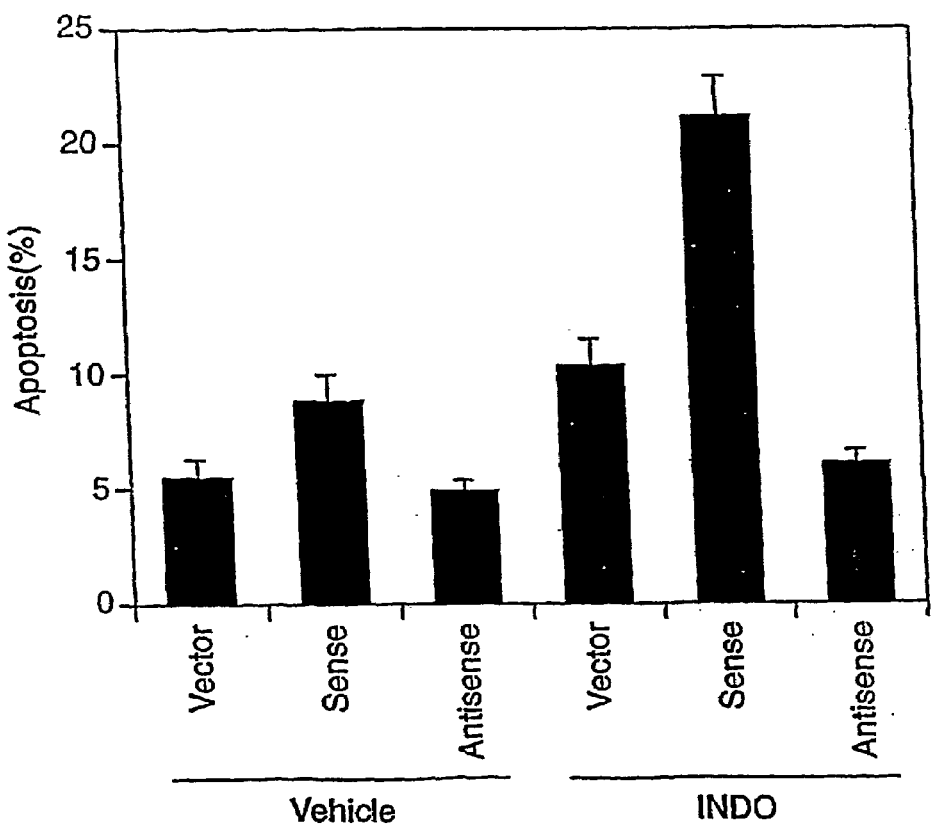

Figure 7
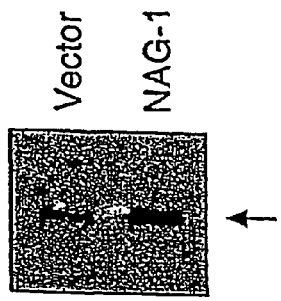
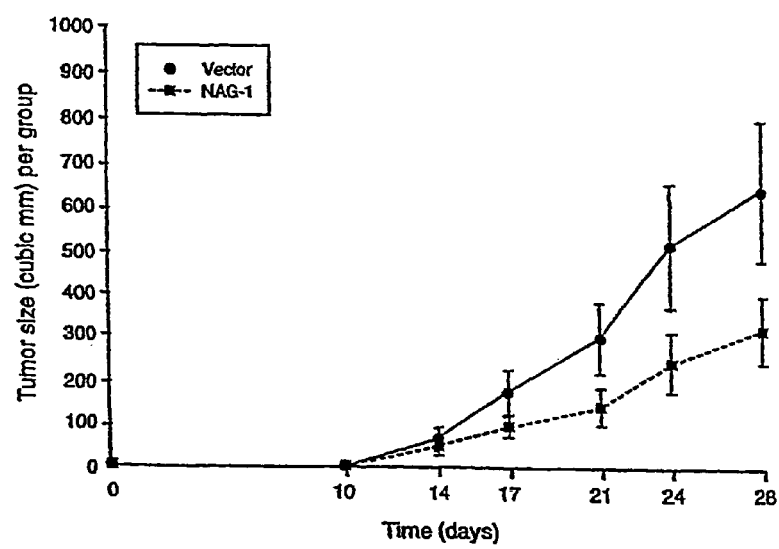
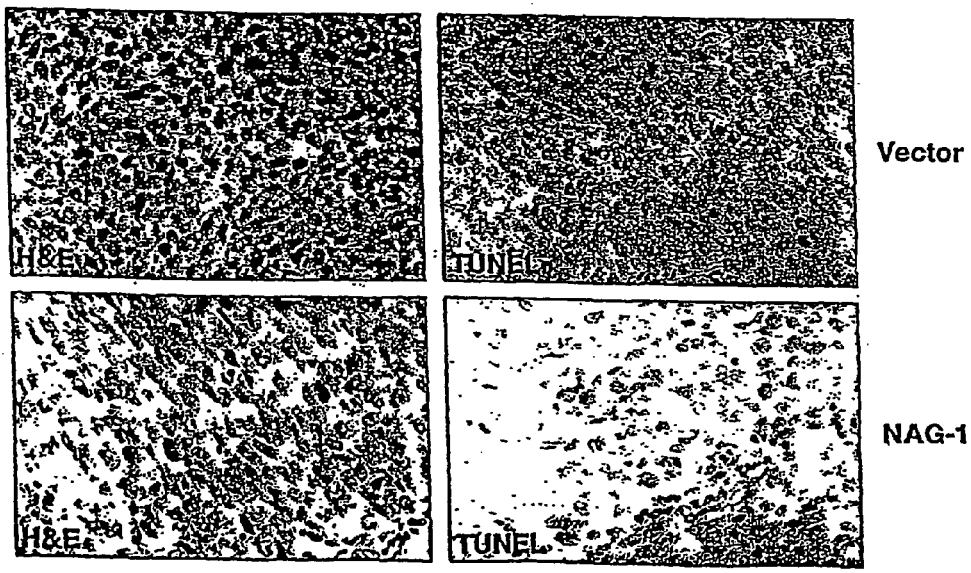

Figure 8

```
nag_PROMOTER  Length: 8902  July 28, 2000 10:50  Type: N  Check: 2018

1  GAATTCGAGC TCGGTACCCG GGGATCGATC CTCTAGAGTC GACCTGCAGG
  51  CATGCAAGCT TGCGGCCGCC CTAGGACTAG TCTCGAGGCT AGCCCATGGG
 101  GCGCCGGGCC CGGATCACCT GAGGTCCGGA GTTCGAGATC AGCCTGGGCA
 151  ACACGGTGAA ACCCCGTCT CTACTAAAAA TTCAAAAATT AGCTGGGCAT
 201  GGTGGTGCAT GCCTGTAATC CCAGCTACTC GGGAGGCTAA GGCAGGAGAA
 251  TCGTTTGAAC CCAGGAGGTG GAGACTGCAG TGAGTCGAGA TGGCGCCATT
 301  GCACTCCAGC CTGGGCAACA AGAGTAAATC TCCATCTCAC AAAAAAAAA
 351  AAAAAAAGCA AGGCACAGTG GCATCAGGCT GGGGTGGGAA GATCACTTGA
 401  GCCCAGCCAT TCGAGACCAA CCTGTGCAAC ACAGGAAAAC CCCATTCTAC
 451  AAAATAGTAA AAAATTATCA GGGCATGGTG GCACATGCCT ATAGTCCCAG
 501  CTACTCGGGA GAGTGATGGG GGAGGATCAC TTGAGCCCAG GAGGTCGAGG
 551  CTGCGGTGAC CTATGATTGT GCCACTGCAC TCCAGCCTGG GCTACACAGC
 601  CAGACCCTGT CTAAAAGAA ACAAACAGG CAGGACGCGG TGGCTCACAC
 651  CTGTAATCCC AGCACTTTGG GAGGCCGAGG TGGGCGGATC ACCTGACATC
 701  AGGAGTTCGA GACCAGCCTG TCCAACATCG TGAAATCCCC CTCTCTACTA
 751  AAATACAAAC ATTAACCGGG CATGGTAGTG GGTGCCTGTA ATCCTACCTA
 801  CTCGGGAGGC TGAGGCAGGA AAATTGCTTG AACCTGGGAG ATGGAGGTTG
 851  CAATGAGCCG AGATCGCGCC ACTGCACGAC AGCCTAGGCG ACAGAACAAG
 901  ACTCCATCTC AAAAAAAAA GAAAAGAAA AAAGAAGAA ACTCTCATTG
 951  ATGGGTGTTC ATTGATGGAG CACTTTTTGG GAATGGGTTG ACATGCTCAC
1001  AGTGTTTTTA ACCTCACCTC GTCTCTGAAG AGGTGCAGAT AAAAGTCACC
1051  TGGTGAGGAA AATGCCTTTT TAAAAACAAT TTTTAGAGGG CCAGCACGGT
1101  GACTCACGAC TGTAATCTGA GCAATTTGGG AGGCCGAGGT GGGCGGATCA
1151  CTTGAGGTCA GGAGTTCAAA ACCAGTCTGG CCAACATGGT GAAATCCTGT
1201  CTCTACTAAA AATACAAAAA TTAGTTGGGC ATGGTGGCAC ATGCCTGTAA
1251  TCCCAGCTAC TCGGGAAGCT GAGGCAGGAG AATCACTTTA ACCCAGGAGG
1301  TGGAAGTTGC AGTGAGCCAA GATCGCGCCA GTGCACTCCA GCCTGGGCAA
1351  CAGAGCGAGA CTCTGTCTCA AAGAAAAAA AAAAGAGATG GGGTCTTGGG
1401  GTCTCACTGT GTTGCCCAGG CTGGTCTCCA ACTCCTGGCC TCAAGCAATC
1451  CTCCTGCTTT GGCCTCCCAA AGTGCTAGGA TTACATGCCT GAGCCACTGT
1501  GTTCAACCAG GGTGTCCCTT TTCTGAGACT GCATTCTTCC CACCTTGCCC
```

Figure 8 (cont.)

```
1551  AAGTATTGCA GGAGAAACAC AAGCCCCATG CTGTGCTGGC GAAATCTCAT
1601  CTCATGCTGG CCTGTTAGGG TGGCCATATC CTCTCATTTC AAGAGGCTCT
1651  GAGGGAGATG AACAGGCTC AGCGGCTGGC TGCTTGGGC TCTAACCCCA
1701  GCCCTGCTGT CTTCTGGCTG TGTGGCCGTG ACGAGCCCAC CTCTCTGGCC
1751  TCAGTTTGTC ATCTGTGAAA TGGACATAAT CTATCCACCA CATCAGGCTG
1801  TATAAAGATT AGGCCAGGTG TGGTGCCTCA CACCTGTAAT CCCAGCGCTT
1851  TGGGAGGCTG AGGCAGGCAG ATCACCTAAG GTCAGGAGTT CGAGACCAAC
1901  CTGGCCAAAA TGGTGAAACC CTGTCTCTAA TAAAAATACA AAAATTAGCT
1951  GGGCATGGTG GCATGTACCT GTAATCCCAG CTACCCAGGA GGCTGAGGCA
2001  GGAGAATCGC TGGAACCCGG GAGGCAGAGG CTGCAGTGAG CCAAGATTGC
2051  ACCACTGCAC TCCAGCCTGA GTGACAGAGC GAAACTCCGT CTCAGAGAAA
2101  AAAAAAAAAA AAAAGATAT GTCCAACTCC TAACGCTCAG TATCTGTGAC
2151  CTTATTTGGA AAGAAGGTCT TTGCAAATGT AATTAAACTA AAGATCTTGT
2201  ACTGAGATCA TTCTGAATTA AAAATGGACC CGTGGCTGGG CACAGTGGCT
2251  CACACCTGTA ATCCCAGCAC TCTGGGAGGC TGAGGTGGGC AAATCACCTG
2301  AAATCAGGAG TTCAAAACCA GCCTGGCCAA CATGGCGAAA CCCCGTCTCT
2351  ACTAAAAATA CAAAAAAAAA TTAGCTGGGC GTTGTGGTGC ACACCTGTAA
2401  TTCCAGCTAC TCGGGAGGCT GAGGCAGGAG AATCACTTGA ACCTGGGAGG
2451  CTGCAGTGAG CCGAGATTGC GCCACTGCAT TCCAGCCTAG GCAACAAGAG
2501  TGAAACTCTG TCTCGAAAAT AAAAACATAA GAAAGAGTGG ACCCATGGCC
2551  AGGCACAGTG GCTCATGCCT ATAATCCCAA CACTTTGGGA GGCCAAGATG
2601  GAAAGATCGT TTGAACTCAG CCGTTTGAAA CCAGCCTGGG CAACATAGTG
2651  AGACCCTGTG TCTAAATACA AACACAAACA GAAAACAAAA AGAACCCGGG
2701  CTGGCTGCGG AACCCCCTAG ATGGCACAGG CACATCCGGG CTTTCGAGGA
2751  CAGTCACGAG CATGAGACAG CATTTCTTCT TGTCCTCGGG GCCTGCAGGA
2801  AGTTTTTAAG TAATCTGCTT TTGTGCCTCT TCCAAATCTC CTCCTATGAC
2851  CCTGTTTACC TTACATCACA AGAAACAATC AATAAAAGTG GTTTGTGTTC
2901  GTGAGTGCCG TGTGTTTGAC AAAGGCGTTG ATAACTGAGA GCTGGTAGTG
2951  GAGGGGGGAG ATTTTGGGAG ATTGGGCCC TGCCAGGTGG ACGGACTGGC
3001  CTGACCTCCG GCCCTGCGC TCTGTTTACT TCCATCCCAG CTCCACCTCT
3051  GGGGACCCAT GGAAGCTGTC GGTGAGGAAC ACAGGATCCG ACCTGCTGAG
3101  CTCATCTCTG GCCACCTGCC TGCATCCGCC CCATCTCTCC TCTCAGCTTG
```

Figure 8 (cont.)

```
3151  GCCATGAGGC GGGCTATGAG GTCATTGGTT AAAGATTTGG GGAAGCAGAG
3201  CCAGGCGAGT GGCCAGATGT GGTGGCTCAT GCCATCACAG GATCCAGCAC
3251  TGTGAGAGGA CAAGGAAGGA GGATCCTTGA CCTCAGGAGT TCAAAACCAG
3301  CCTGTACAAC ATAGCAAGAC CCCGTCTCT ACAAAATATA AAATTAACCA
3351  GTTGTGGAGG CACGCGCCTC TATTCCCAAC TACTCGGGAG GTTGAGGTGA
3401  CAGGATCCCT TGACCCAGGA GGTCGAGGCT GCATTGAGTG GGTAACAGAG
3451  CCAAACCCTG TCTCTAAAAC AAACAAAACA GAAACAAAAA GTACACTACT
3501  TACTGTCCTG CTTCTCACCA TTCCAGCCTG GGTAGTCCTT TTTTTTTTTT
3551  TTGAGACAGG GTCTTGCTCA TTGCTCAGGC TGGAGTGCAG AAGCGTAATC
3601  ACAGCTCACT GCAGCCTTGA TCTCCAAAAA GACTACCAGC TTGGCTGGGT
3651  GTGGGACTC ATGCCTATAA CCCCAGCATT TTGGGAGCCA GAGGCAAGAG
3701  GATTCCTTGA GCCAAGGAGT TCGAGACCAG CCTGGGCAAC ACAGTGAGAC
3751  CCTATCTCTA AAATTTTTT TTTTGAGATG GAATTTAGCT CTCATTGCCC
3801  AGGCTAGAGT GCAATGGTGC AATCTCAGCT CACCACAATC TCCACCTCCC
3851  AGGTTCAAGC AAAATTCTCC TGCCTCAGCC TCCCGAGTAG CTGGGATTAC
3901  AGGCATGCGC CACCATGCCC GGCTAATTTT GTTTTTTAAA GAGACGGGGT
3951  TCTCCATGTT GGTCAGGCTG GTCTCAAACT CCCAACCTCA GGTGATCTGC
4001  CTGCCTTGGC CTCCCTATCT CCTCATTGGG GGCCATAGGA TTAAATAGCT
4051  TTTTTCTTTT TTTATGAGAC GGAGTTTCTC TGTGTCCCAC AGGTTGGAGG
4101  CAGTGGCACA ATCACGGCTC ACGGCAACCT CCGCCTCCTG CCTCAGCCTA
4151  CTGAGTAGCT GGGATTACAG TCATGCGCCA CCACATCTGG CCATCTTGTG
4201  TGTTTGAGTA ATCTCGGTAT ATATCCATTT TGTCTATGAA GCTCGTTAAT
4251  TTGGGCCCCA AAGCACCCGC TGGCAATGGC CTTTAAGTGC GAAAATCCTG
4301  GCATTAGGCG TCCCCCACCT TTTTTTTTTT TTTTGTTGG GACGGATGTA
4351  GGTGTGTCGC CCAGGCTGGA GTGCAGTGGC GCAATCTCGG CTCACTGCAA
4401  GCTCCGCCTT CCGGGTTCAC GCCTTTCTCC CACCTCAGCC TCCCGAGTAG
4451  CTGAGACTAC AGGCACCCAC CACCATGCCT GGCTAATTTT TTTGTATTTT
4501  TAGTAGAGAG GGGGTTTCAC CGTGTTAGCC AGGATGGTCT TGATCTCCTG
4551  ACCTCGTGAT CCGCCTGACC TCGGCCTTCC AAAGTGCTGG GATTACAGGC
4601  AAGAGCCACC GCGCCCGGCC TGGTGTCCTT ATTTCTTGGG AAAGGATACA
4651  GAGGGTCAGA GAGGCGCCCC AGCTTGTGCA GGAATGCATT CCTGAGATCT
4701  GGCCTGGCCG TGGTCACTGG AGTGTTTACT CTGCTTACAG GGTCTGGTGT
```

Figure 8 (cont.)

```
4751  AGTGGGGGAT GGCTGGGTAG GAACGTGCGG GCTATAAAGC CAGACCCCAG
4801  GTGTCAGTGC GGTTCAGAAA GCAACTAGCA CAGCCATGCC CAGGCCAGGA
4851  CCCGTGACAC AGCGATGCTC TCAGATGCTG CTGATGTTAC AGATGTTGTT
4901  GGGGGCACCC TGACTCTGCA GGTGAGACCT TCTGGGTTCC TAGGACCCTT
4951  GGACAAGCAC TTTGATCCGG ATGACTCCAG GTCCCAGGAG TTGCAGAAAC
5001  GCCACGAGGA CTTTCAGAGC CCCAGTTAGA CAAGGAGAGC CCAGGAGGAG
5051  TTGGCCCCCA CCCTCATCCC AAAAGCACAG GTGAGCTTTG AGACCTCCCA
5101  CCCCCAGGAC AGCCCCCATG TCTATTTTCT TTTTCTTTAA AGATGTTCTT
5151  ATTTGGGGGC CCAGGCGTGG TGGCTCATGC CTGTAATCCC AGCACTTTGG
5201  GAGGCCGAGG CAGGCGGATC ACCTGAGATC AGGAGTTCGA GACCAGACTG
5251  GCCAACATGA CAGGGTGAGA CCCCATCTTT ACAACAAATA CAAAAATTAC
5301  CCAGGCATGG TGGCACACGC CTGTAATCCC AGCTACTAGG GAGGATGAAG
5351  CAGGAGAATT GCTTGAACCC GGGAGGCGGA GATTGTAGTG AGTTGAGATC
5401  GCACAACTGC ACTCCAGCCT GGGCAACAGA GGGAGACTCC AATCCAAAAA
5451  AAAGAAAAAA ATCCCCTAGG ACAGGGCTGT GGCTGAGACC CTGAGGGCTG
5501  GAGGCTTGGC TGGCCTTGCA CAGCAGCGGG TGCATGCTGG GGTGGGGAGA
5551  GGCCTGGAGA CCCTGTGACT CCACTGGGGG CCTTGCTGTG TGACCCCCTA
5601  GTGAGTCCTT GTGTCTCTTA CCCACGCATG CCTGTCACAT GCAGACACCC
5651  ACACACACCC AGTATCTGCC GGACAGGGCA GCCCTTCCTC TCCGCAGCCA
5701  GGAAGCTGGA CATAGGCACA AGGGCTGACG CCTGGGGCCA GGAATCCTGC
5751  CTGAGCATTA GGATAAGGTC TGGGAACCCC AGGGGGAAGG GCACTCCTGG
5801  GGCATCCCCT GCCCCTCTAC CATCTGGTGG GCTTGGACTC TTACACCAAG
5851  CCTGCCCTGC TCTAAAACCC CACTCTCAAT TCTGTGCCAC CTCCTCTCTG
5901  GGCCCAGACA AGAGCAGATT CATCCCTGCC CCAAAGGAAC CACCAGTCTT
5951  GGGTCAGCAG AGCTGGGCAC AGACACTTCC AGTGCCGTGG GGCTGTAACT
6001  GTGATAGGTC TGTTGCTCCA TGCACTTGGC AAGTCAACAG CTGAGAAAAC
6051  AGGTTGCAAC ATGGAAAGAG TTTTAATCCG ACCGGCGTGG TGGCTCATGC
6101  CTGTAATCCC AGCACTTTGG GAGGCTGAGG CGGGTGGATC ATCTGAGGCC
6151  AGCAGTTCAA GATCAGCCTG GCCAACCAGG TGAAACCTCA TCTCTACTAA
6201  AAATACAAAA ATTAGCCAGG CGTGATGGTG CGCACCTGTA ATCCCAGCTA
6251  CTTGGGAGGC TGAGGCAGGA GAATCAATTG AACCTGGGAG GCGGAGGTTG
6301  CAGTGAGCCA AGATCATACC ACTGCACTCC AGCCTGGGCA ACAGAGCGAG
```

Figure 8 (cont.)

```
6351  AGACTGTCTC GGAAGAAAAA AAAAAAAAAA AGGCTGGGGG CAGTGGCTCA
6401  TGCCTGTAAT CCCCACACTT TAAAGGCAGA GGCCGACGGA TGACTTGAGG
6451  TCAAGAGTTC GAGACCTGCC TGGCAACATG GTGAATCACC GTCTCTACTA
6501  AAAACACAAA ATTAGCCAGG TGTGGTGGCG CATGACTGTA ATCCCAGCTA
6551  CTCAGTAGGC TGAGGCAGGA GGCGGAGGTT GCAGTGAGCC GAGATTGTGC
6601  CACTGCACTC CAACCTGGGG GACAGAGAGA AACTCCGTCT CAAAAAAAA
6651  AAAAAAAGA GATTTAATCC TAGGGCCACC CAATGAGGAG ATAGGAGGGA
6701  ACCTCAAATC CATTTCCAGG AGGAGGAGTT TGGGGCCATA TAAATGTATA
6751  TATACAAATA TATATATATT TTTAAGATGG AGTCAGCCGG CCGTGGTGGC
6801  TCACGCCTCT AATCCCAATA CTTTGGGAGG CCGAGGCCGG CGGATCACAA
6851  GGTCAGGAGA TTGAGACCAT CTTAGCTAAC ACGGTGAAAC CCCATCTCTA
6901  CTAAAAATAC AAAAAAAAT TAGCCAGGCG TGGTGGGGGG TGATCATAGT
6951  CCCAGCTACT CAGGAGGTTG AGGCAGGAGA ATAGCATGAA CCTGGGAGCT
7001  GGAGCTTGCA GGTTGGAGTG CAATGGCATG ATCTCAGCTC AATGCACCTC
7051  CGCCTCCTGG TTCAGCGATT TCTCCTGCCT CAGGCTCCCG AGCAGCTGGG
7101  ATTACAGGCA TGTGCCCACC ACGACCGGTT AATTTCTGAA TTTTTTAGTA
7151  GAGACAGGTT TCATCATGTT GTCAGGCTGG TCTCGAACTC CTGACCTCAG
7201  GTGATCCGCC CGCCTTGGCC TCCCAAAGTG CTGGGATTAC AGGCGTGAGC
7251  CACTGCACCT GGCCAGGGGC TAGAGTTTTA ATTTTTAAGG ATTTTGGAGT
7301  GGGCTGAAGT GTGGAGGTCA TTGCTTGGTG AAAGAGTGCA GGAGGTGAAG
7351  TCACAGACAG TAAGAAACTG TATTCTCATG CAGATTCCGT TCCTCTGTGG
7401  GGTCTTCACA CTGGTGGGTG TCATTGGTTA AGGATTTCAA AAACATCTTA
7451  AGAAATTCTT CTAAAAAGTC TTATGATTCT AAGGTCGGAA ATCACATCTA
7501  TAGCAAATGG TCGGTATCAG GTGCTACAAG CAACTTGCGG TCACAAGGAA
7551  GTGGGTCAAA GTGCAGCCTG ATTAGTGCTT AATTATAACT AAGTTTCTGT
7601  CCAGAATTCT TTTTTTTTGA GACAGAGTTT TGCTCTTGTT GATCAGGCGG
7651  AAGTGCAATG GTGAAAACTT GGCTCACTGC AACCTCCGCC CTCTGGGTTC
7701  AAGCGATTCT CTTGCTTCAG CCTCTCGAAT AGCTGGGATT ACAGGCATGT
7751  AATCCCACCA CCAAGCCCAG CTAATTTTGT ATATTTAGTA GAGACAGGGT
7801  TTCTCCATGT TGGTCAGGCT AGtctagaac tcttgacgtc agatgatcca
7851  cgtgcctcgg cctcccaaag tgctgggatt acaggcgaga gccaccgtgc
7901  ccggcgcaga attctttttt ttagagatga ggtattgcca tcttgcccag
```

Figure 8 (cont.)

```
7951  acttgtctcg aactcctggg ctcaaacaat ccacccacct cggcctccca
8001  aagtgctgag attactgaca taagccacca tgcctggccc ccagaattat
8051  gaatcctgtg aggatggctt caaggtgagc gctgagccag acaaaaggat
8101  ggggtttggg agcaccctgc ttagactgga aagataatgt tggagaagac
8151  ttcctggaag aggggctttt tgcgtagagt tttgaagaat gagtaggagt
8201  tctccagagg aggatgagta actgcaataa cacccagttt atcaagtgcc
8251  tcctatgtgt ctggccctgt gctttacccc tcatttgacc acctctccag
8301  tgagagtctc agtccttttt ttcctggtga ggaaacaggc atggcagaga
8351  ggcatgacac atcaaggttg cccttcctgg ctccatctag cccgttctcc
8401  tctgcttcct ttgtttttca ccatctttag cctttgaccc caaccaaaaa
8451  gagaagagag gaaatcccat gggcatagac agccacctct taaactcttg
8501  tctggaattt ttcacatagt aacaatgtct ttttttcctc caaaaagact
8551  cccaggctgg aatggtgtcc tcatatcgag gaagaggata ctgaggccca
8601  gaaatgtgcc ctagctttac taggagcgcc cccacctaaa gatcctcccc
8651  ctaaatacac ccccagaccc cgcccagctg tggtcattgg agtgtttact
8701  ctgcaggcag ggggaggagg gcgggactga gcaggcggag acggacaaag
8751  tccggggact ataaaggccg gtccggcagc atctggtcag tcccagctca
8801  gagccgcaac ctgcacagcc atgcccgggc aagaactcag gacggtgaat
8851  ggctctcaga tgctcctggt gttgctggtg ctctcgtggc tgccgcatgg
8901  gg
```

Figure 9 under review

NON-STEROIDAL ANTI-INFLAMMATORY DRUG ACTIVATED GENE WITH ANTI-TUMORIGENIC PROPERTIES

This patent application claims the benefit of U.S. Provisional Patent Application No. 60/231,246, filed Sep. 8, 2000.

FIELD OF THE INVENTION

This invention generally relates to drug screens for agents that are agonistic or antagonistic to activation of the promoter region of the NAG-1 gene.

BACKGROUND OF THE INVENTION

Nonsteroidal anti-inflammatory drugs (NSAIDs) are widely used in the treatment of inflammatory disease. Their anti-inflammatory effects are believed to result from their ability to inhibit the formation of prostaglandins by prostaglandin H synthase (COX). Two isoforms of prostaglandin H synthase, COX-1 and COX-2 have been identified. COX-1 is constitutively expressed in many tissues, while the expression of COX-2 is regulated by mitogens, tumor promoters, and growth factors. High expression of COX-2 has been reported in human colorectal tumors and tumors from other tissues, suggesting a role for this enzyme in regulating tumor growth. NSAIDs are effective in reducing human and rodent colorectal, and possibly, breast and lung cancer. In addition, retrospective and prospective studies link NSAID usage to a reduced risk for colorectal cancer death. NSAIDs are effective in reducing the number and size of polyps in animal models, and epidemiological studies indicate that use of NSAIDs provide a 40–50% reduction in mortality from colorectal cancer.

Our understanding of the mechanisms by which NSAIDs exert their anti-tumor effect is not clear. One possible mechanism is altered arachidonic acid (AA) metabolism, since NSAIDs inhibit the formation of prostaglandins by COX-1 and COX-2. Recent data suggest that inhibition of COX by NSAIDs may increase the cellular pool of AA, resulting in the hydrolysis of sphingomyelin to ceramide, which promotes apoptosis. Some data link NSAID chemoprevention in colorectal cancer cells to prevention of angiogenesis and induction of apoptosis. COX appears to regulate angiogenesis induced by colon cancer cells and NSAIDs appear to limit tumor growth. In epithelial cells of the intestinal crypt, elevated COX-2 expression appears to attenuate apoptosis. Some evidence links NSAID-induced apoptosis to inhibition of COX, but other data suggest a prostaglandin-independent mechanism for the induction of apoptosis. PPARγ agonists also have anti-tumorigenic activity and stimulate apoptosis. For example, ligand activation of PPARγ inhibits proliferation of breast cancer cells, and the addition of PPARγ ligands to cancer cells induces apoptosis. PPARγ agonists also inhibit the growth of transplantable tumors in a nude mouse model.

As is evident from the foregoing, NSAIDs, and the pathways they activate, have great potential for use in the war against cancer. However, as is also evident from the above, insufficient information has been available regarding the NSAID-induced or associated anti-cancer pathways, to help identify agents that are potentially advantageous as cancer treatments. What is needed are novel reagents and methods that can be used to screen for compounds that show promise as anti-cancer agents.

SUMMARY OF THE INVENTION

The present invention generally relates to compositions and methods of identifying and testing NAG-1 gene-activating agonists and antagonists. Activation of the NAG-1 gene by NSAIDs has been correlated with the apoptotic elimination of certain types of cancer cells. Although not limited to any particular mechanism, one embodiment of the present invention involves the use of the promoter region of the NAG-1 gene to test for agents that are agonistic or antagonistic to promoter activation. In this regard, test kits also constitute an embodiment of the present invention. In addition, the invention provides methods to identify other members of the NAG-1 gene family, methods to identify homologs of NAG-1 which are native to other tissue or cell types and methods to generate reagents derived from the invention.

The present invention is not limited by the method of the employed screen. In one embodiment, the present invention contemplates screening suspected compounds in a system utilizing transfected cell lines. In one preferred embodiment, the cells are transfected transiently, while in another preferred embodiment, the cells are stably transfected. In yet another preferred embodiment, transgenic animals are generated. In yet another embodiment, high throughput screens are contemplated. For example, the present invention provides means to screen compound libraries, peptide libraries and the like, in order to identify suitable antagonists or agonists.

The present invention also contemplates the use of a reporter gene construct operationally linked to the NAG-1 promoter. The present invention is not limited to any particular reporter gene construct, as many reporter gene constructs will find use with the present invention. For example, in a preferred embodiment, a luciferase reporter gene is used. In other embodiments, genes encoding fluorescent proteins (e.g., green fluorescent protein), β-galactosidase, or proteins that may be precipitated (e.g., by immunoprecipitation) are used.

It is further contemplated that the present invention will find use in the identification of native activators or inhibitors of the NAG-1 gene. For example, it is contemplated that peptide libraries produced from native genes are screened by the present invention. Non-natively occurring peptides are also be screened by the present invention. In another embodiment, combinatorial libraries are screened. In yet another embodiment, mixtures of compounds are screened. In some preferred embodiments, if a compound mixture gives a positive test result, the mixture is then subdivided into constitutory components and retested. In still further embodiments, this procedure is repeated until the active component or components are identified.

The present invention also be finds use in the identification of new homologs of NAG-1, as well as genes that share similarities in the promoter region or natural mutations thereof. The present invention contemplates screening for homologs using standard molecular procedures. In one preferred embodiment, screens are conducted using Northern and Southern blotting.

Furthermore, as shown in Example 8 below, the NAG-1 peptide has anti-tumor and pro-apoptotic effects. It is contemplated that this peptide, or a portion thereof, will be effective in the treatment of certain cancers when administered directly to tumors or to cancer patients. In this regard, the present invention also provides compositions and methods for the use of the NAG-1 peptide for the treatment of cancers. The present invention further provides the compositions and methods for use of modified or derived variations of the NAG-1 peptide for the treatment of cancers.

The present invention is not limited to the treatment of any particular cancer as it is contemplated that all cancers may be treated with the NAG-1 peptide. The present invention is also not limited to any particular portion of the NAG-1 peptide for the treatment of cancers, as it is contemplated that any suitable portion of the NAG-1 peptide will find use in cancer treatment. Furthermore, the present invention is not limited to any particular modification of the NAG-1 peptide for the treatment of cancer. Indeed, any modification that changes the ability of the NAG-1 peptide to treat cancer is embodied in the present invention. Such changes include, but are not limited to, increased stability, increased solubility, increased tumor killing ability, decreased toxicity, increased half-life before and after administration to the patient, etc. Also, the present invention is not limited to any particular method of administration, as the NAG-1 peptide may be administered by any suitable means including, but not limited to, oral, nasal, intravenous, intramuscular, intrathecal and subcutaneous modes of administration. Additionally, the NAG-1 peptide may be administered as an ointment, lotion or gel (i.e., for the treatment of skin and mucosal tumors).

The present invention further provides purified DNA having an oligonucleotide sequence comprising SEQ ID NO:1, as well as compositions comprising this sequence or portion(s) thereof. In addition, the present-invention provides expression vectors comprising at least a portion of the oligonucleotide sequence of SEQ ID NO:1. Further still, the present invention provides compositions comprising the translation product of at least a portion of SEQ ID NO:1. The present invention further provides compositions comprising antibodies reactive with at least a portion of the translation product of SEQ ID NO:1. The present invention also provides transgenic animals generated from an expression vector comprising at least a portion of the oligonucleotide sequence of SEQ ID NO:1.

The present invention provides methods for screening compounds, comprising the steps of: a) providing in any order, cells comprising a recombinant expression vector, wherein the vector comprises at least a portion of the oligonucleotide sequence of SEQ ID NO:1 and at least one reporter construct; and, at least one compound; b) contacting the cells with the compound(s) to produce treated cells; and, c) detecting the readout of the reporter construct or constructs in the treated cells.

The present invention also provides methods for screening compounds, comprising the steps of: a) providing in any order, at least one transgenic animal generated from a recombinant expression vector wherein, the vector comprises at least a portion of the oligonucleotide sequence of SEQ ID NO:1 and at least one reporter construct; and, at least one compound; b) exposing the transgenic animal(s) to at least one compound to produce at least one treated animal; and, c) detecting the readout of the reporter construct(s) in the treated animal(s). The present invention further provides methods wherein, at least one transgenic animal is repeatedly (i.e., more than once) exposed to at least one compound. The present invention also further provides methods wherein the treated animal further comprises cancer cells and a decrease or increase in the number of cancer cells present in the treated animal is measured.

The present invention also provides methods comprising: providing in any order, a patient with symptoms of cancer and, a composition comprising at least a portion of the NAG-1 peptide; and b) administering the composition to the patient. The present invention is not limited to any particular type of cancer as it is contemplated that the present invention will find use with all types of cancer. Additionally, the present invention is not limited to any particular means of administration of NAG-1 to the patient, as the NAG-1 peptide may be administered by any suitable means including, but not limited to, oral, nasal, intravenous, intramuscular, intrathecal and subcutaneous modes of administration. Additionally, the NAG-1 peptide may be administered as an ointment, lotion or gel (i.e., for the treatment of skin and mucosal tumors).

DESCRIPTION OF THE FIGURES

FIG. 1 shows the identification and expression of NAG-1 by INDO. Panel A provides a schematic diagram for reported genes PLAB, PTGFB, PDDF, MIC-1, and HP00269. The bar indicates the coding region of cDNA with amino acids reported previously. Panel B provides Northern and Western analysis results that indicate NAG-1 induction is time-dependent. Panel C is a graph showing the apoptosis and cell cycle kinetics of INDO-treated HCT-116 cells at different time points. Panel D provides Northern and Western data showing the concentration-dependent expression of NAG-1. Panel E is a graph showing the apoptosis and cell-cycle kinetics of INO-treated HCT-116 cells at different concentrations.

FIG. 2 shows NAG-1 induction and NSAID-induced apoptosis by several NSAIDs. Panel A shows results for HCT-116 cells treated with various NSAIDs.1 Panel B is a graph showing the correlation between induction of apoptosis and increased expression of NAG-1.

FIG. 4 shows PPARγ ligands also increase NAG-1 expression. Panel A provides results for $15dPGJ_2$ and TGZ. Panel B provides Northern and Western results indicating the time-dependent expression of NAG-1 mRNA and protein in HCT-116 cells. Panel C is a graph showing the apoptosis and cell cycle kinetics of TGZ-treated HCT-116 cells at different times.

FIG. 5 shows the genomic structure and promoter analysis of NAG-1 in HCT-116 cells. Panel A provides a restriction map of the NAG-1 gene. Panel B is a deletion analysis of the NAG-1 promoter. Panel C is a graph showing the luciferase activity of 2021 bp NAG-1 promoter in the presence of TGZ and various NSAIDs.

FIG. 6 shows ectopic expression of NAG-1 induces apoptosis in vitro. Panel A provides Western analysis of ectopic expression of NAG-1 in HCT-116 cells. Panel B is a graph showing the results for stably transfected HCT-116 cells treated with a vehicle or 100 µM INDO.

FIG. 7 shows that NAG-1 reduces growth rate of tumors in nude mice. Panel A, is a Western blot showing the results for transfected with HCT-116 cells probed with anti-NAG-1 antibody. Panel B is a graph showing the tumor size determined over time. Panel C provides H&E stained and TUNEL tissue sections of the tumor area.

FIG. 8 provides the NAG-1 promoter region. In particular, the 9 kb nucleotide sequence promoter region (SEQ ID NO:1) of the NAG-1 gene (SEQ ID NO:2) is shown. In this Figure, lower case letters represent previously published sequences. The region from 5368 to 8821 is the 3.5 kb region referred to as SEQ ID NO:3. Position 8821 is the translational start point. Position 8788 is the transcriptional start point.

Figure 9:
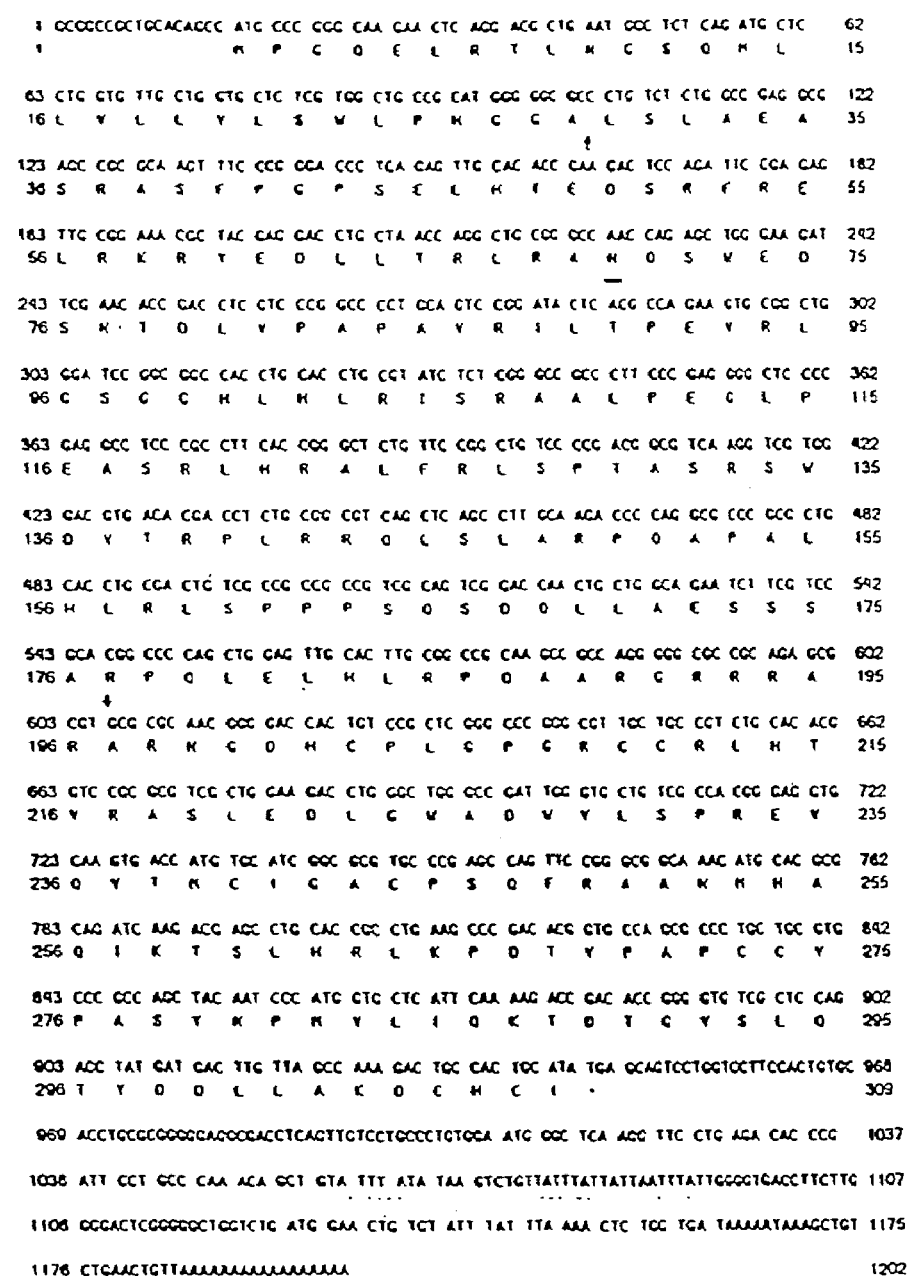

FIG. 9 provides the NAG-1 gene sequence (SEQ ID NO:2; GenBank database accession no. AF019770).

DEFINITIONS

Figure 3:
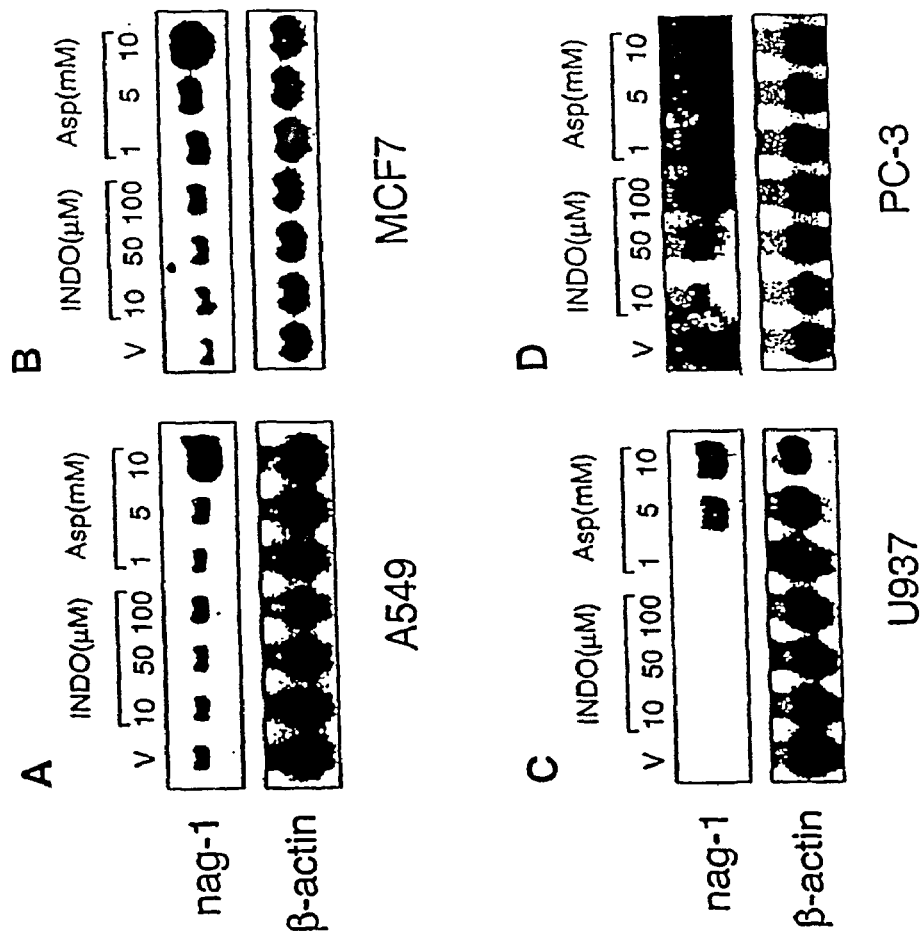
FIG. 3 shows NAG-1 induction by INDO and aspirin in different cell lines. Panel A provides Northern blot results for A549 lung carcinoma cells, while Panel B provides Northern blot results for MCF-7 breast carcinoma cells, Panel C provides Northern blot results for U937 leukemia cells, and Panel D provides Northern blot results for PC-3 prostate cells.

To facilitate understanding of the invention, a number of terms are defined below.

As used herein, the terms "purified" and "to purify" refer to the removal of one or more (undesired) components from a sample. For example, where recombinant polypeptides are expressed in bacterial host cells, the polypeptides are purified by the removal of host cell proteins thereby increasing the percent of recombinant polypeptides in the sample.

As used herein, the term "partially purified" refers to the removal of a moderate portion of the contaminants of a sample to the extent that the substance of interest is recognizable by techniques known to those skilled in the art as accounting for a measurable amount of the mixture.

As used herein, the term "substantially purified" refers to molecules, (e.g., nucleic or amino acid sequences) that are removed from their natural environment, isolated or separated, and are at least 60% free, preferably 75% free, and more preferably 90% free from other components with which they are naturally associated. Furthermore, an "isolated polynucleotide" encompasses a substantially purified polynucleotide.

As used herein "agent," "compound," and "drug," are used herein to denote a mixture of chemical compounds, a biological macromolecule, or an extract made from biological materials such as bacteria, plants, fungi, or animal (particularly mammalian) cells or tissues that are suspected of having therapeutic properties. The compound, agent or drug may be purified, substantially purified or partially purified. Additionally, an "agent," "compound" or "drug" may be substantially pure (i.e., in some cases, comprised of essentially one component).

As used herein "agonist" refers to molecules or compounds which mimic the action of a "native" or "natural" compound. The present invention encompasses agonists that are homologous to these natural compounds, in respect to conformation, charge or other characteristics, as well as compounds that are not homologous. Thus, agonists may or may not be recognized by, for example, receptors expressed on cell surfaces. In any event, regardless of whether the agonist is recognized by a natural compound in a manner similar to a "natural" compound or molecule, in some cases the agonist causes physiologic and/or biochemical changes within the cell (i.e., such that the cell reacts to the presence of the agonist) in the same manner as if the natural compound was present.

As used herein "antagonist" refers to molecules or compounds which inhibit the action of a "native" or "natural" compound. As used herein, "antagonist" also encompasses compounds that are homologous to these natural compounds in respect to conformation, charge or other characteristics, as well as, compounds that are not homologous. Thus, antagonists are recognized by the same or different receptors or molecules as recognized by an agonist. Antagonists may have allosteric effects which prevent the action of an agonist (e.g., by modifying a DNA adduct). In addition, in some cases, antagonists prevent the function of the agonist (e.g., by blocking a DNA repair molecule).

"Patient" as used herein, refers to a human or other animal, such as a guinea pig, mouse, rat, etc. In some preferred embodiments, a patient is treated using the methods and compositions of the present invention.

"Host" as used herein, refers to a recipient cell or organism.

"Transgenic animal" as used herein, refers to a non-human animal having a genetically engineered genotype. In particularly preferred embodiments, transgenic animals are produced by experimental manipulation of the genome of the germline of the non-human animal. Genetically engineered non-human animals may be produced by several methods including the introduction of a "transgene" comprising nucleic acid (usually DNA) into an embryonal target cell or integration into a chromosome of the somatic and/or germ line cells of a non-human animal by way of human intervention, such as by the methods described herein. Non-human animals containing at least one a transgene are referred to as "transgenic non-human animals." Thus, a transgenic animal is an animal whose genome has been altered by the introduction of a transgene. Such non-human animals include vertebrates such as rodents, non-human primates, ovines, bovines, ruminants, lagomorphs, porcines, caprines, equines, canines, felines, aves, etc. Preferred non-human animals are selected from the order Rodentia which includes murines (e.g., rats and mice), most preferably mice.

"Apoptosis" as used herein, refers to the generally recognized term for the morphological changes that are observed in a cell as the cell undergoes a non-accidental death.

"Programmed cell death" as used herein, refers to the genetically controlled process that is executed in a cell that has been induced to undergo apoptosis.

"Antibody" as used herein, refers a glycoprotein produced by B cells and plasma cells that binds with high specificity to an antigen (usually, but not always, a peptide) or a structurally similar antigen, that generated its production. Antibodies may be produced by any of the known methodologies and may be either polyclonal or monoclonal.

"Wild-type," as used herein, refers to a gene or gene product which has the characteristics of that gene or gene product when isolated from a naturally occurring source. A wild-type gene is that which is most frequently observed in a population and is thus arbitrarily designed the "normal" or "wild-type" form of the gene.

"Mutant," as used herein, refers to any changes made to a wild-type nucleotide sequence, either naturally or artificially, that produces a translation product that functions with enhanced or decreased efficiency in at least one of a number of ways including, but not limited to, specificity for various interactive molecules, rate of reaction and longevity of the mutant molecule.

"Staining," as used herein, refers to any number of processes known to those in the field that are used to better visualize a specific component(s) and/or feature(s) of a cell or cells.

"TUNEL" as used herein, refers to terminal deoxynucleotidyl transferase (TdT) mediated FITC-dUTP nick end labeling, a technique to quantitate apoptosis known to those in the field.

The terms "cancerous" and "cancer cell" refer to a cell undergoing early, intermediate or advanced stages of multi-step neoplastic progression as known in the art (See e.g., Pitot, in *Fundamentals of Oncology*, Marcel Dekker (Ed.), New York, pp. 15–28 [1978]). The microscopic features of early, intermediate and advanced stages of neoplastic progression have been described. Cancer cells at each of the three stages of neoplastic progression generally have abnormal karyotypes, including translocations, inversion, deletions, isochromosomes, monosomies, and extra chromosomes. A cell in the early stages of malignant progression is referred to as "hyperplagtic cell" and is characterized by dividing without control and/or at a greater rate than a normal cell of the same cell type in the same tissue. Proliferation may be slow or rapid but continues unabated. A cell in the intermediate stages of neoplastic progression is referred to as a "dysplastic cell." A dysplastic cell resembles an immature epithelial cell, is generally spatially disorganized within the tissue and has lost its specialized structures and functions. For example, during the intermediate stages of neoplastic progression, an increasing percentage of the epithelium becomes composed of dysplastic cells. "Hyperplastic" and "dysplastic" cells are referred to as "pre-neoplastic" cells. In the advanced stages of neoplastic progression a dysplastic cell become a "neoplastic" cell. Neoplastic cells are typically invasive. Thus, they either invade adjacent tissues, or are shed from the primary site and circulate through the blood and lymph to other locations in the body where they initiate secondary cancers. The term "cancer" or "neoplasia" refers to a plurality of cancer cells.

"Nucleic acid sequence," "nucleotide sequence" and "polynucleotide sequence" as used herein, refer to an oligonucleotide or polynucleotide, and fragments or portions thereof, and to DNA or RNA of genomic or synthetic origin which may be single- or double-stranded, and represent the sense or antisense strand.

As used herein, the terms "oligonucleotides" and "oligomers" refer to a nucleic acid sequence of at least about 10 nucleotides and as many as about 60 nucleotides, preferably about 15 to 30 nucleotides, and more preferably about 20–25 nucleotides, which can be used as a probe or amplifier.

The term "nucleotide sequence of interest" refers to any nucleotide sequence, the manipulation of which may be deemed desirable for any reason, by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences that do not encode an mRNA or protein product (e.g., promoter sequences, enhancer sequences, polyadenylation sequences, termination sequences, etc.).

"Amino acid sequence," "polypeptide sequence," "peptide sequence," and "peptide" are used interchangeably herein to refer to a sequence of amino acids.

A "variant" of a nucleotide sequence is defined as a nucleotide sequence which differs from the referenced, parent or wild type nucleotide sequence (e.g., by having one or more deletions, insertions, or substitutions that may be detected using hybridization assays or using DNA sequencing). Included within this definition is the detection of alterations to the genomic sequence of the nucleotide sequence. For example, hybridization assays may be used to detect alterations in: (1) the pattern of restriction enzyme fragments capable of hybridizing to a genomic sequence of the first nucleotide sequence (i.e., RFLP analysis); (2) the inability of a selected portion of the first nucleotide sequence to hybridize to a sample of genomic DNA which contains the first nucleotide sequence (e.g., using allele-specific oligonucleotide probes); and (3) improper or unexpected hybridization, such as hybridization to a locus other than the normal chromosomal locus for the first nucleotide sequence (e.g., using fluorescent ill situ hybridization (FISH) to metaphase chromosomes spreads, etc.). One example of a variant is a mutated wild type sequence.

The term "portion" when used in reference to a nucleotide sequence refers to fragments of that nucleotide sequence. The fragments may range in size from 5 nucleotide residues to the entire nucleotide sequence minus one nucleic acid residue.

DNA molecules are said to have "5'ends" and "3'ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide is referred to as the "5"end" if its 5' phosphate is not linked to the 3' oxygen of a mononucleotide pentose ring. An end of an oligonucleotide is referred to as the "3'end" if its 3' oxygen is not linked to a 5' phosphate of another mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects that transcription proceeds in a 5' to 3' direction along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

The term "recombinant DNA molecule" as used herein refers to a DNA molecule which is comprised of segments of DNA joined together by means of molecular biological techniques.

The term "recombinant protein" or "recombinant polypeptide" as used herein refers to a protein molecule which is expressed using a recombinant DNA molecule.

As used herein, the terms "vector" and "vehicle" are used interchangeably in reference to nucleic acid molecules that transfer DNA segment(s) from one cell to another.

The terms "expression vector," "expression construct," "expression cassette" and "plasmid," as used herein refer to a recombinant nucleic acid molecule containing a desired coding sequence and appropriate nucleic acid sequences necessary for the expression of the operably linked coding sequence in a particular host organism. The sequences may be either double or single-stranded. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The terms also refer to the linkage of amino acid sequences in such a manner so that a functional protein is produced.

"Reporter construct," "reporter gene," and "reporter protein," as used herein, refer to nucleic acid or amino acid sequences, as appropriate, that, when expressed in a host cell or organism, may be detected, measured or quantitated.

The term "transfection" as used herein refers to the introduction of foreign nucleic acid (e.g., DNA) into cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, biolistics (i.e., particle bombardment) and the like.

As used herein, the terms "complementary" or "complementarity" are used in reference to "polynucleotides" and "oligonucleotides" (which are interchangeable terms that refer to a sequence of nucleotides) related by the base-pairing rules. For example, the sequence "5'-CAGT-3'," is complementary to the sequence "5'-ACTG-3'." Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands may have significant effects on the efficiency and strength of hybridization between nucleic acid strands. This may be of particular importance in amplification reactions, as well as detection methods which depend upon binding between nucleic acids.

The terms "homology" and "homologous" as used herein in reference to nucleotide sequences refer to a degree of complementarity with other nucleotide sequences. There may be partial homology or complete homology (i.e., identity). A nucleotide sequence which is partially complementary (i.e., "substantially homologous") to a nucleic acid sequence is one that at least partially inhibits a completely complementary sequence from hybridizing to a target nucleic acid sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding the probe will not hybridize to the second non-complementary target.

In preferred embodiments, an oligonucleotide sequence which is a "homolog" of a first nucleotide sequence is an oligonucleotide sequence which exhibits greater than or equal to 50% identity, and more preferably greater than or equal to 70% identity, to the first nucleotide sequence, when sequences having a length of 10 bp or larger are compared.

As used herein, the term "hybridization" is used in reference to the pairing of complementary nucleic acids using any process by which a strand of nucleic acid joins with a complementary strand through base pairing to form a hybridization complex. Hybridization and the strength of hybridization (i.e., the strength of the association between the nucleic acids) is impacted by such factors as the degree of complementarity between the nucleic acids, stringency of the conditions involved, the $T_m$ of the formed hybrid, and the G:C ratio within the nucleic acids.

As used herein the term "hybridization complex" refers to a complex formed between two nucleic acid sequences by virtue of the formation of hydrogen bounds between complementary G and C bases and between complementary A and T bases; these hydrogen bonds may be further stabilized by base stacking interactions. The two complementary nucleic acid sequences hydrogen bond in an anti-parallel configuration. A hybridization complex may be formed in solution (e.g., $C_0t$ or $R_0t$ analysis) or between one nucleic acid sequence present in solution and another nucleic acid sequence immobilized to a solid support (e.g., a nylon membrane or a nitrocellulose filter as employed in Southern and Northern blotting, dot blotting or a glass slide as employed in in situ hybridization, including FISH (fluorescent in situ hybridization)).

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in *Nucleic Acid Hybridization* [1985]). Other references include more sophisticated computations which take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. "Stringency" typically occurs in a range from about $T_m° $ C. to about 20° C. to 25° C. below $T_m$. As will be understood by those of skill in the art, a stringent hybridization can be used to identify or detect identical polynucleotide sequences or to identify or detect similar or related polynucleotide sequences. Under "stringent conditions" the nucleotide sequence of SEQ ID NO:1, SEQ ID NO:2, SEQ ID NO:3, SEQ ID NO:4 and SEQ ID NO:5, or portions thereof, will hybridize to its exact complement and closely related sequences.

Low stringency conditions comprise conditions equivalent to binding or hybridization at 68° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5× Denhardt's reagent (50× Denhardt's contains per 500 ml: 5 g Ficoll (Type 400, Pharmacia), 5 g BSA (Fraction V; Sigma)) and 100 µg/ml denatured salmon sperm DNA followed by washing in a solution comprising 2.0×SSPE, 0.1% SDS at room temperature when a probe of about 100 to about 1000 nucleotides in length is employed.

It is well known in the art that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol), as well as components of the hybridization solution may be varied to generate conditions of low stringency hybridization different from, but equivalent to, the above listed conditions. In addition, conditions which promote hybridization under conditions of high stringency (e.g., increasing the temperature of the hybridization and/or wash steps, the use of formamide in the hybridization solution, etc.) are well known in the art. High stringency conditions, when used in reference to nucleic acid hybridization, comprise conditions equivalent to binding or hybridization at 68° C. in a solution consisting of 5×SSPE, 1% SDS, 5× Denhardt's reagent and 100 µg/ml denatured salmon sperm DNA followed by washing in a solution comprising 0.1×SSPE and 0.1% SDS at 68° C. when a probe of about 100 to about 1000 nucleotides in length is employed.

When used in reference to a double-stranded nucleic acid sequence such as a cDNA or genomic clone, the term "substantially homologous" refers to any probe which can hybridize either partially or completely to either or both strands of the double-stranded nucleic acid sequence under conditions of low stringency as described above.

When used in reference to a single-stranded nucleic acid sequence, the term "substantially homologous" refers to any probe which can hybridize (i.e., it is the complement of) the single-stranded nucleic acid sequence under conditions of low stringency as described above.

The term "heterologous nucleic acid sequence" or "heterologous DNA" are used interchangeably to refer to a nucleotide sequence which is ligated to a nucleic acid sequence to which it is not ligated in nature, or to which it is ligated at a different location in nature. Heterologous DNA is not endogenous to the cell into which it is introduced, but has been obtained from another cell. Generally, although not necessarily, such heterologous DNA encodes RNA and proteins that are not normally produced by the cell into which it is expressed. Examples of heterologous DNA include reporter genes, transcriptional and translational regulatory sequences, selectable marker proteins (e.g., proteins which confer drug resistance), etc.

"Amplification" is defined herein as the production of additional copies of a nucleic acid sequence and is generally carried out using polymerase chain reaction technologies well known in the art (See e.g., Dieffenbach and Dveksler, *PCR Primer, a Laboratory Manual*, Cold Spring Harbor Press, Plainview N.Y. [1995]). As used herein, the term "polymerase chain reaction" ("PCR") refers to the methods of U.S. Pat. Nos. 4,683,195, 4,683,202, and 4,965,188, all of which are hereby incorporated by reference, and which describe a method for increasing the concentration of a segment of a target sequence in a mixture of genomic DNA without cloning or purification. The length of the amplified segment of the desired target sequence is determined by the relative positions of two oligonucleotide primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

The terms "reverse transcription polymerase chain reaction" and "RT-PCR" refer to a method for reverse transcription of an RNA sequence to generate a mixture of cDNA sequences, followed by increasing the concentration of a desired segment of the transcribed cDNA sequences in the mixture without cloning or purification. Typically, RNA is reverse transcribed using a single primer (e.g., an oligo-dT primer) prior to PCR amplification of the desired segment of the transcribed DNA using two primers.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and of an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that it is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the terms "restriction endonucleases" and "restriction enzymes" refer to bacterial enzymes, each of which cut double- or single-stranded nucleic acid at or near a specific nucleotide sequence.

As used herein, the term "an oligonucleotide having a nucleotide sequence encoding a gene" means a nucleic acid sequence comprising the coding region of a gene (i.e. the nucleic acid sequence which encodes a gene product). The coding region may be present in either a cDNA, genomic DNA or RNA form. When present in a DNA form, the oligonucleotide may be single-stranded (i.e., the sense strand) or double-stranded. Suitable control elements (e.g., enhancers, promoters, splice junctions, polyadenylation signals, etc.) may be placed in close proximity to the coding region of the gene, if needed to permit proper initiation of transcription and/or correct processing of the primary RNA transcript. Alternatively, the coding region utilized in the expression vectors of the present invention may contain endogenous enhancers, splice junctions, intervening sequences, polyadenylation signals, or other sequences, or a combination of both endogenous and exogenous control elements.

Transcriptional control signals in eukaryotes comprise "enhancer" elements. Enhancers consist of short arrays of DNA sequences that interact specifically with cellular proteins involved in transcription (Maniatis et al., Science 236:1237 [1987]). Enhancer elements have been isolated from a variety of eukaryotic sources including genes in plant, yeast, insect and mammalian cells and viruses. The selection of a particular enhancer depends on what cell type is to be used to express the protein of interest.

The presence of "splicing signals" on an expression vector often results in higher levels of expression of the recombinant transcript. Splicing signals mediate the removal of introns from the primary RNA transcript and consist of a splice donor and acceptor site (Sambrook, et al., *Molecular Cloning: A Laboratory Manual*, 2nd ed., Cold Spring Harbor Laboratory Press, New York, pp. 16.7–16.8 [1989]). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is isolated from one gene and placed 3' of another gene.

The terms "promoter," "promoter element," and "promoter sequence" as used herein, refer to a DNA sequence which when placed at the 5' end of (i.e., precedes) an oligonucleotide sequence is capable of controlling the transcription of the oligonucleotide sequence into mRNA. A promoter is typically located 5' (i.e., upstream) of an oligonucleotide sequence whose transcription into mRNA it controls, and provides a site for specific binding by RNA polymerase and for initiation of transcription.

The term "promoter activity" when made in reference to a nucleic acid sequence refers to the ability of the nucleic acid sequence to initiate transcription of an oligonucleotide sequence into mRNA.

As used herein, the terms "nucleic acid molecule encoding," "nucleotide encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The term "isolated" when used in relation to a nucleic acid (e.g., "an isolated oligonucleotide") refers to a nucleic acid sequence that is separated from at least one contaminant nucleic acid with which it is ordinarily associated in its natural source. Isolated nucleic acid is nucleic acid present in a form or setting that is different from that in which it is found in nature. In contrast, non-isolated nucleic acids are nucleic acids such as DNA and RNA which are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs which encode a multitude of proteins. However, isolated nucleic acid encoding a polypeptide of interest includes, by way of example, such nucleic acid in cells ordinarily expressing the polypeptide of interest where the nucleic acid is in a chromosomal or extrachromosomal location different from that of natural cells, or is otherwise flanked by a different nucleic acid sequence than that found in nature. The isolated nucleic acid or oligonucleotide may be present in single-stranded or double-stranded form. Isolated nucleic acid can be readily identified (if desired) by a variety of techniques (e.g., hybridization, dot blotting, etc.). When an isolated nucleic acid or oligonucleotide is to be utilized to express a protein, the oligonucleotide will contain at a minimum the sense or coding strand (i.e., the oligonucleotide may be single-stranded). Alternatively, it may contain both the sense and anti-sense strands (i.e., the oligonucleotide may be double-stranded).

As used herein the term "coding region" when used in reference to a structural gene refers to the nucleotide sequences which encode the amino acids found in the nascent polypeptide as a result of translation of a mRNA molecule. The coding region is bounded, in eukaryotes, on the 5' side by the nucleotide triplet "ATG" which encodes the initiator methionine and on the 3' side by one of the three triplets which specify stop codons (i.e., TAA, TAG, TGA).

As used herein, the terms "structural gene" and "structural nucleotide sequence" refer to a DNA sequence coding for RNA or a protein which does not control the expression of other genes. In contrast, a "regulatory gene" or "regulatory sequence" is a structural gene which encodes products (e.g., transcription factors) which control the expression of other genes.

As used herein, the term "regulatory element" refers to a genetic element which controls some aspect of the expression of nucleic acid sequences. For example, a promoter is a regulatory element which facilitates the initiation of transcription of an operably linked coding region. Other regulatory elements include splicing signals, polyadenylation signals, termination signals, etc.

As used herein, the term "gene" means the deoxyribonucleotide sequences comprising the coding region of a structural gene. A "gene" may also include non-translated sequences located adjacent to the coding region on both the 5' and 3' ends such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into heterogenous nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, post-transcriptional cleavage and polyadenylation.

A "non-human animal" refers to any animal which is not a human and includes vertebrates such as rodents, non-human primates, ovines, bovines, ruminants, lagomorphs, porcines, caprines, equines, canines, felines, aves, etc. Preferred non-human animals are selected from the order Rodentia.

A "transformed cell" is a cell or cell line that has acquired the ability to grow in cell culture for many multiple generations, the ability to grow in soft agar and the ability to not have cell growth inhibited by cell-to-cell contact. In this regard, transformation refers to the introduction of foreign genetic material into a cell or organism. Transformation may be accomplished by any method known which permits the successful introduction of nucleic acids into cells and which results in the expression of the introduced nucleic acid. "Transformation" includes but is not limited to such methods as transfection, microinjection, electroporation, and lipofection (liposome-mediated gene transfer). Transformation may be accomplished through use of any expression vector. For example, the use of baculovirus to introduce foreign nucleic acid into insect cells is contemplated. The term "transformation" also includes methods such as P-element mediated germline transformation of whole insects. Additionally, transformation refers to cells that have been transformed naturally, usually through genetic mutation.

GENERAL DESCRIPTION OF THE INVENTION

The present invention provides methods and compositions for the screening of compounds for agonistic or antagonistic activity and means of activation of the NAG-1 gene promoter region. Nonsteroidal anti-inflammatory drugs (NSAIDs) are known to activate this gene and activation of this gene by NSAIDs correlates with the apoptotic elimination of certain cancers. The present invention provides easy-to-use drug screens that allow for the identification of compounds contemplated to have anti-cancer properties via the activation of NAG-1. It is contemplated that the present invention will facilitate the identification of compounds that are more effective and efficient in the elimination of cancer than currently used anti-cancer compounds.

Currently, NSAIDs are widely used in the treatment of inflammatory disease (See e.g., Vane and Botting, "Mechanism of action of nonsteroidal anti-inflammatory drugs" *Am J Med* 104:2S-8S, 1998). Although the present invention is not limited to any particular mechanism, the anti-inflammatory effects of NSAIDs are believed to result from their ability to inhibit the formation of prostaglandins by prostaglandin H synthase (COX). As discussed above, two isoforms of prostaglandin H synthase, COX-1 and COX-2 have been identified. COX-1 is constitutively expressed in many tissues, while the expression of COX-2 is regulated by mitogens, tumor promoters, and growth factors (Herschman, "Prostaglandin synthase 2" *Biochim Biophys Acta* 1299:125–140, 1996). High expression of COX-2 has been reported in human colorectal tumors and tumors from other tissues, suggesting a role for this enzyme in regulating tumor growth. NSAIDs are effective in reducing human and rodent colorectal, and possibly, breast and lung cancer (Castonguay et al., "Inhibition of lung tumorigenesis by NSAIDS: a working hypothesis" *Exp Lung Res* 24:605–615, 1998; Han et al., "Effects of sulindac and its metabolites on growth and apoptosis in human mammary epithelial and breast carcinoma cell lines" *Breast Cancer Res Treat* 48:195–203, 1998; Taketo, "Cyclooxygenase-2 inhibitors in tumerogenesis (Part I)" *J Natl Cancer Inst* 90:1529–1536, 1998; Taketo, "Cyclooxygenase-2 inhibitors in tumerogenesis (Part II)" *J Natl Cancer Inst* 90:1609–1620, 1998). In addition, retrospective and prospective studies link NSAID usage to a reduced risk for colorectal cancer death. NSAIDs are effective in reducing the number and size of polyps in animal models, and epidemiological studies indicate that use of NSAIDs provide a 40–50% reduction in mortality from colorectal cancer (Boolbol et al., "Cyclooxygenase-2 overexpression and tumor formation are blocked by sulindac in a murine model of familial adenomatous polyposis" *Cancer Res* 56:2556–2560, 1996; Thun et al., "Aspirin use and risk of fatal cancer [see comments]" *Cancer Res* 53:1322–1327, 1993).

As discussed above, our understanding of the mechanisms by which NSAIDs exert their anti-tumor effect is not clear. One possible mechanism is altered arachidonic acid (AA) metabolism, since NSAIDs inhibit the formation of prostaglandins by COX-1 and COX-2. However, an understanding of the mechanism(s) is not necessary in order to use the present invention. Recent data suggest that inhibition of COX by NSAIDs may increase the cellular pool of AA, resulting in the hydrolysis of sphingomyelin to ceramide, which promotes apoptosis (Chan, "Mechanism underlying nonsteroidal antiinflammatory drug-mediated apoptosis" *Proc Natl Acad Sci* 94:11514–11519, 1998). Some data link NSAID chemoprevention in colorectal cancer cells to prevention of angiogenesis and induction of apoptosis. COX appears to regulate angiogenesis induced by colon cancer cells and NSAIDs appear to limit tumor growth (Tsujii et al., "Cyclooxygenase regulates angiogenesis induced by colon cancer cells [published erratum appears in Cell 1998 Jul. 24:94(2): following p271]" *Cell* 93:705–716, 1998). In epithelial cells of the intestinal crypt, elevated COX-2 expression appears to attenuate apoptosis (Tsujii and DuBois, "Alteration in cellular adhesion and apoptosis in epithelial cells overexpressing prostaglandin endoperoide synthase 2" *Cell* 83:493–501, 1995). Some evidence links NSAID-induced apoptosis to inhibition of COX, but other data suggest a prostaglandin-independent mechanism for the induction of apoptosis (Hanif et al., "Effects of nonsteroidal anti-inflammatory drugs on proliferation and on induction of apoptosis in colon cancer cells by a prostaglandin-independent pathway" *Biochem Pharmacol* 52:237–245, 1996; Murphy et al., "Cyclooxygenase-2-selective antagonists do not inhibit growth of colorectal carcinoma cell lines" *Cancer Lett* 122:25–30, 1998). PPARγ agonists also have antitumorigenic activity and stimulate apoptosis. Ligand activation of PPARγ inhibits proliferation of breast cancer cells (Mueller et al., "Terminal differential of human breast cancer through PPAR gamma" *Mol Cell* 1:465470, 1998). The addition of PPARγ ligands to cancer cells induce apoptosis (Bishop-Bailey and H1a, "Endothelial cell apoptosis induced by the peroxisome proliferator-activated receptor (PPAR) ligand 15-deoxy-delta12, 14-prostaglandin J2" *J Biol Chem* 274:17042–17048, 1999; Chinetti et al., "Activation of proliferative-activated receptors alpha and gamma induces apoptosis of human monocyte-derived macrophages" *J Biol Chem* 273:25573–25580, 1998; Elstner et al., "Ligands for peroxisome proliferator-activated receptor gamma and retinoic acid receptor inhibit growth and induce apoptosis of human breast cancer cells in vito and in BNX mice" *Natl Proc Acad Sci USA* 95:8806–8811, 1998; Keelan et al., "15-deoxy-delta (12, 14)-prostaglandin J(2), a ligand for peroxisome proliferator-activated receptor-gamma, induces apoptosis in JEG3 choriocarcinoma cells" *Biochem Biophys Res Commun* 262:579–585, 1999; Takahashi et al., "Activated of PPAR gamma inhibits cell growth and induces apoptosis in human gastric cancer cells" *FEBS Lett* 455:

135–139, 1999). PPARγ agonists also inhibit the growth of transplantable tumors in a nude mouse model (Clay et al., "Influence of J series prostaglandins on apoptosis and tumorigenesis of breast cancer cells" *Carcinogenesis* 20:1905–1911, 1999).

Until the development of the present invention, the stimulation of the expression of proteins that have both anti-inflammatory and anti-tumorigenic activity by NSAIDS and/or PPARγ ligands was not previously determined. As detailed in the Experimental section below, NSAID-inducible genes were identified by suppression subtractive hybridization (Diatchenko et al., "Suppression subtractive hybridization: A method for generating differentially regulated or tissue-specific cDNA probes and libraries" *Proc Natl Acad Sci USA* 93:6025–6030, 1996) utilizing the human colorectal adenocarcinoma cell line, HCT-116. NSAIDs and PPARγ ligands were found to increase the expression of a novel member of the transforming growth factor-b (TGF-b) superfamily (NSAID Activated Gene, NAG-1). The expression of this protein is strongly associated with NSAID-induced (or PPARγ-induced) ligand-induced apoptosis in colorectal cells. Furthermore, transplantable tumors derived from over-expressing-NAG-1 HCT-116 cells were found to grow at a slower rate in athymic nude mice than control cells, providing additional evidence for the anti-tumorigenic activity of NAG-1.

As indicated above, the present invention provides methods and compositions for identifying and testing agonists and antagonists of NAG-1 promoter activation and inhibition. Additionally, the invention provides methods and compositions comprising drugs, drug therapies and gene therapies that allow for the elimination or reduction of cancers.

A. Measurement Of Apoptosis—General Indicators

Although an understanding of the mechanism of the invention is not necessary in order to use the present invention, it is contemplated that one of the methods by which NAG-1 activation may eliminate cancer cells is through the process of cell death called apoptosis. Programmed cell death, or apoptosis, is the genetically controlled, systematic dismantling of a cell. Apoptosis typically happens during embryogenesis when much tissue remodeling is taking place, but continues to happen throughout the life of an organism. For example, the elimination of senescent cells, the involution of tissues and the elimination of diseased cells occurs through apoptosis. The hallmarks of the apoptotic process are morphological changes consisting of chromatin condensation, membrane blebbing, loss of membrane integrity and, ultimately, the disintegration of the cell into apoptotic bodies that are engulfed by phagocytic cells. On the molecular scale, DNA is cleaved into 180–200 kb nucleosomal fragments resulting in a laddering appearance when run on an agarose gel. Apoptosis prevents the release of cellular constituents into the extracellular space thereby preventing an inflammatory response and allows for the orderly remodeling of tissues. In contrast, necrotic or accidental cell death is exemplified by membrane rupture and the release of cellular constituents into the extracellular space often resulting in an inflammatory response by the body.

Traditionally, the measurement of apoptosis has involved delineating the percentage of a cell population undergoing apoptosis. However, determining the earliest detectable point in which apoptosis could be accurately detected and determining the kinetics of the apoptotic process have been problematic. The changes in morphology and the DNA laddering discussed above, although not overly quantitative, are the classic determinants of apoptosis. Other measures of apoptosis include, but are not limited to, terminal deoxynucleotidyl transferase (TdT)-mediated FITC-dUTP nick end labeling (TUNEL) staining (indicative of early DNA strand cutting by endonucleases), trypan blue staining (and various other vital stains indicative of loss of membrane integrity), propidium iodide (and various other DNA intercalating dyes indicative of loss of DNA from the nucleus) and Annexin-V staining (indicative of phosphatidyl serine exposure on the cell surface). These techniques allow for better quantitative analysis of apoptosis on a population level but do little to allow for the measurement of the effect of agonists or antagonists on a specific apoptotic signaling pathway.

B. Measurement of Apoptosis—Cell Pathway Specific Techniques

As indicated above, an understanding of the mechanism is not necessary in order to use the present invention. However, some advances have been made into delineating pathway involvement in the apoptotic process. In this regard, inhibitors have been made which target some constituents of the apoptotic pathway. For example, tetra-peptide inhibitors have been developed for several of the caspases activated during apoptosis. Likewise, loss of function and gain of function gene mutants have been made for several steps in the apoptotic process. Additionally, reagents have been developed which combine a fluorogenic substrate with caspase cleavage sites allowing for the visualization of apoptosis-induced caspase activation by flow cytometric methods. These previously developed reagents, however, focus on the pro-apoptotic pathways and fail to look at survival pathways.

C. Advances Conferred by the Present Invention

The present invention provides numerous advantages over the presently available methods for identifying, characterizing, and using drug and gene therapies for cancer treatment. For example, it is contemplated that the present invention will find use in such areas as the design and execution of screens to identify protein or small molecules that interfere with or augment the activation or inhibition of the NAG-1 promoter, as well as the development of therapeutic protocols involving the use of (i) compounds that regulate NAG-1 promoter activation or inhibition and (ii) the establishment of drug and gene therapies for the treatment of various cancers. Other uses of the present invention will be apparent to those in the art.

D. Format of the Present Invention

1. Cell Based Assays

One embodiment of the present invention provides compositions and methods for the transfection of cell lines with plasmids containing the NAG-1 promoter operationally linked to a reporter gene or genes. These cells are then used in tests to measure the effect of test compounds on apoptosis. Empty plasmids are used as controls in some embodiments. In some embodiments, the cells are transiently transfected, while in other embodiments, the cells are stably transfected. However, it is contemplated that stably transfected cell lines allow for more reliable enterozoa comparisons. In preferred embodiments, the indication of promoter activation by the reporter gene identifies compounds suitable for further screening as potential anti-cancer agents (e.g., in transgenic animal-based assays) as outlined below.

2. Transgenic Animal Based Assays

The present invention also provides compositions and methods for the generation of transgenic animals that express reporter genes activated by the NAG-1 promoter, thereby providing in vivo assay systems for screening of potential drug candidates. As these embodiments of the present invention allow for the testing of agents in vivo, they facilitate determinations of potential side effects of tested agents and the ability of the agents to eliminate or reduce cancers. In preferred embodiments, the expression of the reporter gene allows for the generation of data regarding the mechanisms and locations of action of the test compound.

3. Molecular Biological Based Assays

In a further embodiment, the present invention provides compositions and methods for the production of NAG-1 promoter cDNA and RNA. This makes facilitates the performance of a wide range of standard molecular biological assays including, but not limited to, Northern and Southern blotting, PCR, cloning and various screening assays for the detection of intraspecific and interspecific homologs. Thus, the present invention provides many advantages for the identification, development, and utilization of compounds as anti-cancer agents.

DETAILED DESCRIPTION OF THE INVENTION

Generally, the nomenclature used herein, and the laboratory procedures in cell culture, molecular genetics, and nucleic acid chemistry and hybridization described below, are those well known and commonly employed in the art. Standard techniques are used for recombinant nucleic acid methods, polynucleotide synthesis, and microbial culture and transformation (e.g., electroporation, lipofection). Generally enzymatic reactions and purification steps are performed according to the manufacturer's specifications. The techniques and procedures are generally performed according to conventional methods in the art and various general references (See generally, Sambrook, et al., *Molecular Cloning: A Laboratory Manual,* 2d ed., Cold Spring Harbor Laboratory Press, Cold Spring Harbor, N.Y. (1989), and *Current Protocols in Molecular Biology,* John Wiley and Sons, Inc., N.Y. (1996), both of which are incorporated herein by reference).

Oligonucleotides can be synthesized by any means known in the art including, but not limited to, use of an oligonucleotide synthesizer (e.g., Applied BioSystems), according to specifications provided by the manufacturer. Complementary oligonucleotides are annealed by heating them to 90° C. in a solution of 10 mM Tris-HCl buffer (pH 8.0) containing NaCl (200 mM) and then allowing them to cool slowly to room temperature.

Any suitable assays for detecting the ability of agents to inhibit or enhance NAG-1 promoter region activity that provide for facile high-throughput screening of agent banks (e.g., compound libraries, peptide libraries, and the like) will find use with the present invention to identify suitable antagonists or agonists. It is contemplated that such NAG-1 promoter region activity antagonists and agonists will be further developed as therapeutics and diagnostic or prognostic tools for diverse types of cancers, autoimmune diseases and hereditary diseases.

A. Screens to Identify Agonists of Antagonists of the NAG-1 Promoter

There are several different approaches provided by the present invention to confirm the ability of small molecules to specifically inhibit or enhance activation of the NAG-1 promoter. One approach is to transfect expression constructs (i.e., constructs containing the NAG-1 promoter operationally linked to a reporter gene) into cells and measure changes in the expression of the reporter gene as compared to controls transfected with empty constructs after the cells have been exposed to at least one compound. In these screens, the cells are either transiently transfected or stably transfected. Furthermore, transgenic animals allow for in vivo assays to be conducted.

1. In Vitro Assays

Transfection assays allow for a great deal of flexibility in assay development. The wide range of commercially available transfection vectors and reporter constructs permit the expression of NAG-1 components in an extensive number of cell types. In one particularly preferred embodiment, cells are transiently transfected with an expression construct that includes the NAG-1 promotor and a luciferase gene allowing for the detection of NAG-1 promoter activation. In these embodiments, cells are exposed to the agent suspected of modulating NAG-1 promoter activation, and luciferase expression is turned on. Rates of luciferase expression in cells expressing the construct are compared to cells transfected with an empty expression vector. Rates of luciferase activation are then quantitated by any of a number of ways reported in the literature and known to those in the art.

In another preferred embodiment, stably transfected cells lines are developed. The use of various reporter genes allows for numerous types of assays depending on the organism used. Screening assays for compounds suspected of modulating NAG-1 promoter activity are conducted in the same manner as in the transient transfection assays. Using stably transfected cell lines allows for greater consistency between experiments and allow for inter-experimental comparisons.

2. In Vivo Assays

In another embodiment, transgenic animals are constructed using standard protocols. The generation of transgenic animals allows for the investigation of compounds that function by activating the NAG-1 promoter in vivo.

B. Screens to Identify NAG-1 Promoter Homologs

In yet other embodiments, standard molecular biological techniques are used to identify NAG-1 promoter homologs in humans and other species. For example, preferred embodiments include, but are not limited to, DNA-DNA hybridization techniques (e.g. Southern blots) and DNA-RNA hybridization techniques (e.g. Northern blots), as well as other suitable methods.

Experimental

The following examples serve to illustrate certain preferred embodiments and aspects of the present invention and are not to be constructed as limiting the scope thereof.

In the experimental disclosure which follows, the following abbreviations apply: ° C. (degrees Centigrade); $H_2O$ (water); aa (amino acid); bp (base pair); kb (kilobase pair); kD (kilodaltons); gm (grams); µg (micrograms); mg (milligrams); ng (nanograms); µl (microliters); ml (milliliters); mm (millimeters); nm (nanometers); µm (micrometer); M (molar); mM (millimolar); µM (micromolar); nM (nanomolar); sec (seconds); min(s) (minute/minutes); hr(s) and h (hour/hours); ab and Ab (antibody); FITC (fluorescein isothiocyanate); PAGE (polyacrylamide gel electrophoresis); PBS (phosphate buffered saline); SDS (sodium dodecyl sulfate); Tris (tris(hydroxymethyl)aminomethane); EDTA (Ethylenediaminetetraacetic Acid); w/v (weight to volume); v/v (volume to volume); RT (room temperature); S.D. (standard deviation); S.E. (standard error); FACS (fluorescence activated cell sorter); Millipore (Millipore, Bedford, Mass.); Sigma (Sigma Chemical Co., St. Louis, Mo.); Biofluids (Biofluids, Rockville, Md.); Pharmacia (Pharmacia Biotech, Uppsala, Sweden); Dupont/NEN (NEN Life Science Products, Boston, Mass.); Promega (Promega, Madison, Wis.); Becton Dickinson (Becton Dickinson, San Jose, Calif.); Cayman Chemical (Ann Arbor, Mich.); Clontech (Clontech, Palo Alto, Calif.); and Life Technologies (Life Technologies, Bethesda, Md.); ATCC. (Manassas, Va.); Cayman Chemical (Ann Arbor, Mich.); New England BioLabs (Beverly, Mass.); Ambion (Austin, Tex.); Scion Corp. (Frederick, Md.); Schleicher & Schuell (Keene, N.H.); Amersham Pharmacia Biotech (Piscataway, N.J.); Pfizer (N.Y., N.Y.); Parke-Davis (N.Y., N.Y.); Research Genetics (Huntsville, Ala.); and Trevigen (Gaithersberg, Md.).

EXAMPLE 1

Identification of NSAID-Regulated Gene

Although an understanding of the mechanism is not necessary to use the present invention, this Example describes experiments to determine the possible molecular mechanisms for the anti-tumorigenic activity of NSAIDs. These experiments involved the determination of whether NSAIDs could stimulate the expression of proteins which could participate in both the anti-inflammatory and anti-tumorigenic activity of NSAIDs. Suppression subtractive hybridization methods were used to identify NSAID-inducible proteins. Cell lines used in these experiments were purchased from ATCC (Manassas, Va.).

Human colorectal carcinoma cells, HCT-116 cells, were maintained in McCoy's 5A medium supplemented with 10% fetal bovine serum (FBS) and Gentamicin. A549 human lung epithelial carcinoma cells, and U937 human monocytic cells were grown in RPMI 1640 medium supplemented with 10% FBS and Gentamicin. Breast cancer cells, MCF-7 cells, were grown in EMEM medium with 10% FBS, and PC-3 cells were grown in DMEM/F12 medium supplemented with 10% FBS and Gentamicin. All NSAIDs in this study were purchased from Sigma. Troglitazone (TGZ) was obtained from Parke-Davis, and was reconstituted in DMSO. 15d-PGJ$_2$ was purchased from Cayman Chemical and dissolved in ethanol. All NSAIDs were dissolved in DMSO (Sigma), except Sodium Salicylate was dissolved in PBS.

For this experiment, the human colorectal cell line, HCT-116 was selected, since anti-tumorigenic activity of NSAIDs is linked strongly with human colorectal cancer. As confirmed by Western and HPLC analysis, these cells do not express COX-1 and COX-2 (data not shown). A clone, designated INDO29, was isolated from the indomethacin (INDO)-induced library as follows. mRNAs were isolated from INDO-treated (100 μM) or vehicle-treated (0.2% DMSO) HCT-116 cells using a POLY(A)SPIN™ mRNA isolation kit (New England BioLabs). The cDNA Subtraction kit was used to make the INDO(+) and INDO(−) subtractive libraries according to the manufacturer's protocol (Clontech). A gene containing 159 bp was isolated from the INDO-induced library and designated INDO29. The full-length cDNA containing the entire coding region was isolated by RT-PCR using two primers from PTGFB sequence (GenBank #AF008393); sense strand, 5'-ACCT-GCACAGCCATGCCCGGGCA-3' (SEQ ID NO:4) and anti-sense strand, 5'-CAGTGGAAGGACCAGGACT-GCTC-3' (SEQ ID NO:5), and designated as NAG-1 (NSAID Associated Gene). Characterization of this 159 bp fragment by sequence analysis indicated that INDO29 is identical to the 3' region of a novel TGF-β superfamily gene reported recently by five different groups (FIG. 1A). Each clone is represented as follows: Placenta Bone Morphogenic protein, PLAB (GenBank #U88323); Placenta TGF-.beta., PTGFB (GenBank #AF008303); Prostate Derived Factor, PDF (GenBank #AF003934); Macrophage Inhibitory Cytokine-1, MIC-1 (GenBank #AF019770); novel TGF-β super family, HP00269 (GenBank #AB000584). The black bar labeled INDO29 indicates 159 bp fragment first identified by subtractive hybridization from HCT-116 cells, while "NAG-1" indicates the PCR generated full length cDNA. Although these genes are named differently, sequence analyses revealed that the five genes are almost identical, and belong to the new TGF-β superfamily with unknown function. Specific PCR primers were used to generate a full length clone from HCT-116 cells with sequence identity to the five genes shown in FIG. 1A. As indicated above, this NSAIDs activated-gene was designated "NAG-1".

The sequence of the NAG-1 gene encompasses a novel 5'-promoter region not disclosed with any of the other homologous sequences isolated in these experiments. Briefly, recombinant bacteriophage clones were isolated by the plaque hybridization method, from human genomic chromosome-19 specific library (ATCC). The library was screened using a DNA probe containing 966 bp of the NAG-1 promoter, which was labeled by random priming (Ambion) in the presence of [α-$^{32}$P]dCTP (Du Pont-NEN, 3,000 Ci/mmol). After three rounds of screening, large scale phage DNA was prepared according to the procedures known in the art (See, Helns et al., "A lambda DNA protocol based on purification of phage on DEAE-cellulose" *Methods Enzymol* 153:69–82, 1987) using DEAE-cellulose chromatography. Several λ clones were isolated by genomic library screening. One of the positive clones, λNAG61, is in the schematic diagram, FIG. 5A. Exons are indicated by ■ and the number under the box is the exon number. The bar indicates 3.5 kb SmaI fragment cloned into luciferase vector (pNAG3421). The restriction sites are indicated as follows: E, EcoRI; S, SmaI; X, XbaI. One of positive clones (λNAG61) was purified and found to contain 9 kb NAG-1 promoter (SEQ ID NO:1) and the full-length NAG-1 gene (SEQ ID NO:2). The insert of λNAG61 clone was digested with EcoRI and subcloned into a plasmid vector (pBlue-Script II) for sequencing analysis. In addition, the 3.5 kb SmaI fragment containing NAG-1 promoter was cloned into pGLBasic3 (Promega) luciferase reporter vector and assayed for luciferase activity. The 3.5 kb sequence (SEQ ID NO:3) were deposited to GenBank (AF231408).

EXAMPLE 2

NAG-1 Expression and Apoptosis Induced by Indomethacin is Dose- and Time-Dependent To confirm the increased expression of NAG-1 by INDO, Northern and Western blot analyses were performed using HCT-116 cells treated with 100 μM INDO for varying times, as follows. Upon reaching 60–80% confluence in 10 cm plates, the cells were treated at indicated concentrations and times with either different NSAIDs or PPARγ ligands in the absence of serum. Total RNAs were isolated using TRIzol reagent (Life Technologies) according to the manufacturer's protocol. For Northern blot analysis, 10 mg of total RNA was denatured at 55° C. for 15 min and separated in a 1.2% agarose gel containing 2.2 M formaldehyde, and transferred to Hybond-N membrane (AMERSHAM). After fixing the membrane by UV, blots were prehybridized in hybridization solution (Rapid-hyb buffer, AMERSHAM) for 1 hr at 65° C. followed by hybridization with cDNA labeled with [α-$^{32}$P] dCTP by random primer extension (DECAprimeII kit, Ambion). The probes used were either full-length NAG-1 fragment or PTGFB clone (generously provided by Dr. Bento-Soar of the University of Iowa). After 4 hr incubation at 65° C., the blots were washed once with 2×SSC/0.1% SDS at RT and twice with 0.1×SSC/0.1% SDS at 65° C. Messenger RNA abundance Was estimated by intensities of the hybridization bands of autoradiographs using Scion Image (Scion). Equivalent loading of RNA samples was confirmed by hybridizing the same blot with a $^{32}$P-labeled b-actin probe which recognizes RNA of approximately 2 kb.

The level of secreted NAG-1 was evaluated using Western blot analysis with anti-human-NAG-1 antibody (generously provided by Dr. Paralkar of Pfizer). HCT-116 cells were grown to 60–80% confluency in 10 cm plates followed by 48 hr treatment in the absence of serum with either NSAIDs or TGZ. The media were harvested and concentrated approximately 15-fold using Centriprep 10 concentrators (Amicon). Proteins (30 µg) were separated by 15% SDS-PAGE and transferred for 1 hr onto nitrocellulose membrane (Schleicher & Schuell). The blots were blocked for 1 hr with 5% skim milk in TBS/Tween 0.05%, and probed with anti-NAG-1 antibody (1 µg/ml in TBS-0.2%-Tween20) at 40° C. overnight. After washing, the blots were treated with horseradish peroxidase-conjugated secondary antibody for 1 hr and washed several times. The signal was detected by enhanced chemiluminescence system (AMERSHAM) and autoradiography.

The NAG-1 mRNA expression increased with duration of treatment, with a significant increase in expression observed at 24 hr and a further increase in expression observed at 48 hr of treatment (See, FIG. 1B). The expression of NAG-1 protein also increased with duration of INDO treatment, with a marked increase in expression observed at 36 and 48 hr (See, FIG. 1B), indicating time-dependent induction by INDO. HCT-116 cells were treated with 100 µM INDO in the absence of serum for various times. In FIG. 1B, left panel. 10 µg of total RNA was loaded in each lane. Northern blotting was performed using the NAG-1 probe and reprobed with β-actin probe. The hybridization signals were quantitated using Scion Image software (Scion). Levels of the 1.3 kb NAG-1 transcript were normalized to the levels of β-actin transcripts and represented relative to 0 hr treatment. For the Western analysis, (FIG. 1B, right panel) HCT-116 cells were treated with 100 µM INDO for various times in the absence of serum. The media were harvested and concentrated using the Centriprep column (about 700 µl from 10 µl media). Then, 30 µg of proteins were subjected to 15% SDS-PAGE, transferred to nitrocellulose membrane, and probed with anti-NAG-1 antibody (generously provided by Dr. Paralkar of Pfizer). The signal was detected by ECL reagent (AMERSHAM).

To determine whether NAG-1 gene expression is associated with NSAID-induced apoptosis or altered cell cycle kinetics, flow cytometric analysis of the distribution of cells at various stages of the cell cycle was performed. Apoptosis and cell cycle kinetics of INDO-treated HCT-116 cells were measured at different time points. HCT-116 cells were treated with INDO, stained with PI, and analyzed by flow cytometry. Seven thousand five hundred cells were examined by flow cytometry by gating on an area versus width dot plot to exclude cell debris and cell aggregates. Apoptosis is represented by the fold increase in sub-G1 population over 0 hr treatment. All values represent mean±S.D. A prolonged G1 phase and shortened S phase were observed, which was dependent on the duration of INDO treatment (See, FIG. 1C). The changes in the cell cycle are consistent with the previous report that NSAIDs affect cell cycle progression in colon cancer cells. However, since G1 arrest begins to occur at an earlier time point than NAG-1 protein expression, the cell cycle arrest and NAG-1 induction appear to be independent events. In contrast, increases in NAG-1 protein expression and induction of apoptosis exhibited similar time courses, with a nearly 3-fold increase in apoptosis observed at 36 hr, and a 4.5 fold increase at 60 hr of exposure to INDO (See, FIG. 1C). Furthermore, both induction of apoptosis and the increase in NAG-1 expression were dependent on the concentration of INDO. HCT-116 cells were treated with several concentrations of INDO and the cells harvested at 24 hr for mRNA and 48 hr for protein expression. Apoptosis was measured after 72 hr of INDO exposure, as described below.

The DNA content for NSAIDs, PPARγ ligand, and vehicle treated HCT-116 cells was determined by FACS. Cells were plated at a density of 4×10$^5$ cells/well in 2 ml of medium in 6 well plates, incubated for 16 h, and then treated with NSAIDs or TGZ in the presence of serum. After treatment, the cells were harvested, washed with PBS, fixed by the slow addition of cold 70% ethanol to a total of 1 ml, and stored overnight at 4° C. The fixed cells were pelleted, washed once with PBS, and stained in 1 ml of 20 µg/ml of propidium iodide (PI), 1 mg/ml RNase in PBS for 20 min. Seven thousand five hundred cells were examined by flow cytometry using Becton Dickinson FACSort equipped with CellQuest software, by gating on an area versus width dot plot to exclude cell debris and cell aggregates. Each cell cycle distribution was analyzed by the McCycle program using one cell cycle parameter. Apoptosis was measured based on the level of sub-diploid DNA contained in cells following treatment with NSAIDs or TGZ using CellQuest software.

As a second method to detect apoptosis, TACS™ Annexin-V-FITC kit (Trevigen) was used according to the manufacturer's protocol. Annexin-V has specificity for phosphatidylserine, which becomes asymmetrically distributed on the cell surface during early apoptosis. Annexin-V positive/PI positive and Annexin-V positive/PI negative cell populations were determined as apoptotic populations from the total gated cells. As shown in FIG. 1D and FIG. 1E, stimulation of apoptosis and the increase in NAG-1 mRNA and protein expression were also dependent on the concentration of INDO. HCT-116 cells were grown in varying concentrations of INDO for 24 hr or 48 hr. Results of Northern (left panel) and Western analysis (right panel) for these experiments are shown in FIG. 1D. These analyses were performed as described above. In this figure, "V" indicates 0.2% DMSO. FIG. 1E shows the results of studies to determine apoptosis and cell cycle kinetics of INDO-treated HCT-116 cells at different concentrations. Apoptosis analysis was performed by FACS using HCT-116 cells treated with different concentrations of INDO for 48 hr as described above. These results are supportive of an association between NSAID-induced apoptosis and increased expression of NAG-1 in HCT-116 cells.

EXAMPLE 3

Stimulation of NAG-1 Expression and Apoptosis by Other NSAIDs

To determine whether other NSAIDs increased apoptosis and NAG-1 expression, tests were conducted to determine whether variants of NSAIDs induced NAG-1 gene expression and NSAID-induced apoptosis. Aspirin, ibuprofen, indomethacin, and sulindac sulfide were selected since they are known COX inhibitors. Sulindac, acetaminophen and sodium salicylate were also tested since these drugs are weak COX inhibitors but are reported to induce apoptosis.

HCT-116 cells were treated with different NSAIDs (vehicle, 0.2% DMSO; aspirin, 10 mM; ibuprofen, 1 mM; sodium salicylate, 5 mM; sulindac sulfide, 50 μM; sulindac, 40 μM; acetaminophen, 100 μM) for 24 hr in the absence of serum. Northern analysis was performed using NAG-1 and β-actin as probes. Total RNAs were isolated from NSAID-treated HCT-116 cells after 24 hr treatment and Northern blot was performed using NAG-1 cDNA as a probe (data not shown). Each NSAID was tested at 3 different concentrations and maximally effective doses were chosen. Each of the doses were as follows: aspirin (1, 5, 10 mM); ibuprofen (100, 500, 1000 μM); salicylate (1, 2.5, 5 mM); sulindac sulfide (1, 10, 50 μM); sulindac (10, 20, 40 μM); acetaminophen (10, 50, 100 μM). After 48 hr treatment with NSAIDs in the presence of serum, cells were harvested and assayed as described in FIG. 1C. Apoptosis detected by PI staining was measured by FACS, as known in the art (FIG. 2A; HCT-116 cells were treated with different NSAIDs (vehicle, 0.2% DMSO; Aspirin, 10 mM; Ibuprofen, 1 mM; Sodium Salicylate, 5 mM; Sulindac Sulfide, 50 μM; Sulindac, 40 μM; Acetaminophen, 100 μM) for 24 hr in the absence of serum. Northern analysis was performed using NAG-1 and β-actin as probes. The open bars represent the relative expression of NAG-1 mRNA over the control (vehicle). The hatched bars represent the relative apoptosis ratio over vehicle treatment by PI staining methods. N=3±S.D.).

FACS Annexin-V-FITC was also used to detect apoptosis according to the manufacturer's protocol. Annexin-V positive cell populations were determined as early/late apoptotic populations from the total gated cells. The hatch bars in FIG. 2A represent the relative apoptosis ratio over vehicle treatment by Annexin-V assay. Aspirin, ibuprofen, salicylate and sulindac sulfide treatment increased NAG-1 gene expression by 3–4 fold at the highest concentrations tested, while acetaminophen and sulindac did not induce NAG-1 expression at any concentration (data not shown). Treatment with different NSAIDs increased NAG-1 expression in a concentration-dependent manner in HCT-116 cells. Therefore, the concentrations giving the highest fold increase in NAG-1 expression were chosen to stimulate apoptosis. As shown in FIG. 2B, each NSAID tested that induced NAG-1 also induced apoptosis, suggesting a correlation between apoptosis and NAG-1 expression. The NSAID-induced apoptosis was confirmed by annexin V assay (FIG. 2A, hatched bar), which can detect early apoptotic and late apoptotic/necrotic cell populations. Except for sulindac sulfide, a strong correlation was found between PI staining and Annexin-V assay in the detection of apoptosis. The association between NSAID-induced apoptosis and the increase in NAG-1 expression is more clearly illustrated in FIG. 2B. A strong correlation ($r^2$=0.859) was found to exist between NSAIDs which induce NAG-1 expression and NSAIDs which induce apoptosis in HCT-116 cells. Similar data are presented in Table 1, below.

In the Table below, HCT-116 cells were treated with different NSAIDs (vehicle, 0.2% DMSO) for 24 hr in the absence of serum. Northern analysis was performed using NAG-1 and β-actin as probes. The data represent relative expression of NAG-1 mRNA over the control (1.0). Each NSAID was tested at 3 different concentrations and maximally effective concentration used for apoptosis determination. Apoptosis ratio by PI staining was measured by FACS. After 48 hr treatment with NSAIDs in the presence of serum, cells were harvested and assayed. The data represent relative apoptosis ratio over vehicle treatment by PI staining methods. TACS™ Annexin V-FITC kit was also used to confirm apoptosis.

TABLE 1

NAG-1 Induction and NSAID-Induced Apoptosis

|  | Concentration (μM) Used | NAG-1 Induction (mRNA) Fold | Apoptosis (PI Staining) |
|---|---|---|---|
| Conventional NSAIDs |  |  |  |
| Indomethacin | 10–100 | 2.2 | 2.9 ± 0.121 |
| Sulmdac | 10–40 | 1.5 | 1.1 ± 0.173 |
| Sulindac Sulfone | 100–400 | 1.3 | 1.6 ± 0.043 |
| Sulindac Sulfide | 1–50 | 4.6 | 4.3 ± 0.737 |
| Piroxicam | 200–1000 | 2.5 | 1.9 ± 0.145 |
| Diclofenac | 50–200 | 3.7 | 4.0 ± 0.315 |
| Aspirin | 1,000–10,000 | 3.5 | 3.5 ± 0.451 |
| Ibuprofen | 100–1,000 | 4.5 | 4.3 ± 0.666 |
| Sodium Salicylate | 1,000–5,000 | 3.0 | 1.8 ± 0.252 |
| Acetaminophen | 10–100 | 0.9 | 0.9 ± 0.153 |
| COX-2 Specific Inhibitors |  |  |  |
| NS-398 | 10–100 | 0.9 | 1.029 ± 0.109 |
| DFU | 10–100 | 1.0 | 0.54 ± 0.091 |
| Celecoxib* | 0.01–0.1 | 1.0 | 0.722 ± 0.098 |
| LM-4101 | 10–100 | 3.0 | 4.057 ± 0.119 |
| LM-4108 | 10–100 | 1.0 | 1.7 ± 0.229 |
| LM-4115 | 10–100 | 1.0 | ND# |

*This compound was toxic to the HCT-116 cells at the pM concentration.
ND: Not Determined

EXAMPLE 4

NAG-1 Induction by NSAIDs in Lung, Breast, Leukemia, and Prostate Cells

NSAID-induced apoptosis is not restricted to colorectal cells, as NSAIDs can induce apoptosis in breast, lung, leukemia, and prostate cell lines. To test for the induction of NAG-1 by NSAIDs in different cell lines, A549 lung epithelial cells, MCF-7 mammary cells, PC-3 prostate cancer cells, and U937 leukemia cell lines were treated with several concentrations of INDO and aspirin. Then, as described above, Northern blot analysis was performed. As shown in FIG. 3, NAG-1 was induced in different cell lines, A549 lung carcinoma cells (A), MCF-7 breast carcinoma cells (B), U937 leukemia cells (C), and PC-3 prostate cells (D). Quiescent cells were grown for 24 hr in the presence of indicated NSAIDs. Total RNAs were isolated and subjected to Northern analysis using NAG-1 and β-actin as probes. The blots contained 10 μg of total RNA from INDO- or Aspirin (Asp)-treated cells with indicated doses. "V" indicates total RNAs from vehicle (0.2% DMSO) treated cells. The results shown are representative of those obtained in two experiments.

As shown in FIG. 3, NAG-1 gene expression was induced by INDO or aspirin in all of the cell lines tested. Interestingly, in U937 cells, which did not express basal NAG-1, INDO treatment resulted in only a modest increase in NAG-1 expression, while aspirin (5 mM) significantly increased NAG-1 expression. All of the cell lines tested in these experiments showed high NAG-1 induction by 10 mM Aspirin. Thus, the ability of NSAIDs to increase the expression of NAG-1 is not specific for colorectal cells but is also observed in other cells.

EXAMPLE 5

NAG-1 Induction and Apoptosis by PPARγ Ligands

The absence of COX expression in HCT-116 cells suggested that the induction of NAG-1 by NSAIDs is not linked to inhibition of prostaglandin formation. Although an understanding of the mechanism is not necessary in order to use the present invention, one possible mechanism of NAG-1 induction is through the activation of the peroxisome proliferator-activated receptors, PPARγ and PPARγ. INDO, ibuprofen and other NSAIDs bind to and activate PPARγ and PPARγ (Lehmann, et al., 1997; Ricore, et al., 1998) at similar concentrations used in this investigation. Furthermore, PPARγ is expressed in human colon tumors and several colon cancer cell lines, including HCT-116 cells (DuBois, et al., 1998), and the activation of PPARγ results in growth arrest in colon cancer cells (Brockman, et al., 1998). The observation that NSAIDs activate PPARγ, and PPARγ ligands induce apoptosis and growth arrest in vitro, led to experiments to determine whether conventional PPARγ and PPARγ ligands could increase NAG-I expression in HCT-116 cells. While it was determined that PPARγ ligands were not effective (data not shown), as shown in FIG. 4A, 15-deoxy-$\Delta^{12,14}$-prostaglandin $J_2$ (15d-PGJ$_2$) and Troglitazone (TGZ), PPARγ ligands, induced NAG-1 gene expression in a concentration-dependent manner (3-fold at 1 μM and 5 μM, respectively). Interestingly, TGZ-induced NAG-1 expression was observed at earlier times than were observed after INDO treatment. An increase in NAG-1 mRNA was also observed as early as 3 hr after treatment, and an increase in NAG-1 protein was also observed at 6 hr after treatment with 5 μM TGZ (See, FIG. 4B). Cells were grown in the absence of serum for 16 hr and treated with 5 μM TGZ for varying times. Total RNAs were subjected to Northern analysis and concentrated medium was used for Western analysis as described in Example 1. In FIG. 4C, (black bars) apoptosis is represented by the fold induction of sub GI population over 0 hr treatment. All values represent mean±S.D. To determine whether TGZ also induces apoptosis in HCT-116 cells, FACS analysis was performed (See, FIG. 4C). Cell cycle and apoptosis analyses were performed as described below. HCT-116 cells were plated in 6-well plates at a density of 4×10$^5$ cells/well in 2 ml of medium, incubated for 16 hr, and treated with TGZ (5 μM) in the presence of serum over different time points. G1 arrest was seen at the same time point as INDO treatment (12 hr). However, apoptosis was observed as early as 12 hr after treatment. Interestingly, the apoptosis induced by TGZ was observed at earlier times compared to apoptosis induced by INDO treatment (12 hr and 36 hr, respectively). The stimulation of apoptosis by TGZ is consistent with previous publications reporting that PPARγ ligands cause the induction of apoptosis in a number of colon cell line including HCT-116, in breast cancer cells (MCF7), and in monocyte-derived macrophage cells (U937). Taken together, these results support an association between NAG-1 expression and apoptosis.

EXAMPLE 6

Transcriptional Regulation of NAG-1 by PPARγ Ligands and NSAIDs

To investigate transcriptional activation of NAG-1, the NAG-1 promoter was cloned and examined. A 966 bp PCR fragment corresponding to the 5' end of the human PTGFB was used as a probe to isolate λNAG61, a 17 kb human NAG-1 genomic clone. Southern blot analysis of λNAG61, using this 966 bp fragment as a probe, indicated that the λNAG61 clone contains full-length NAG-1 containing two exons and a 9 kb 5' region of NAG-1 promoter (See, FIG. 5A). In this Figure, exons are indicated by ■ and the number under the box is the exon number. The bar indicates a 3.5 kb SmaI fragment cloned into luciferase vector (pNAG3421). The restriction sites are indicated as follows: E, EcoRI; S, SmaI; X, XbaI.

In other experiments, a BAC clone (BAC182K4) containing NAG-1 gene was purchased from Research Genetics and characterized by Southern analysis. The 3.5 kb SmaI fragment was characterized and found to contain the NAG-1 promoter in both the λNAG61 and the BAC clone. To characterize the human NAG-1 5' flanking region and identify the PPARγ ligand and/or NSAID response element in the NAG-1 promoter, a 3.5 kb fragment containing NAG-I promoter was cloned into luciferase reporter vector, and was transiently transfected into HCT-116 cells.

FIG. 5B shows deletion analysis of the NAG-1 promoter. The pNAG3421 clone was deleted by ExoIII nuclease to generate several deletion clones. The clones were transiently transfected into HCT-116 cells, treated either with TGZ (10 μM), or INDO (100 μM), and the luciferase activity was measured after 24 hr treatment. The number next to the clone names in FIG. 5B indicates the length (bp) of the promoter. The data presented in this Figure represent the mean±S.D. of the relative luciferase activity of the test compared with that obtained with the vehicle treated-pNAG474 clone, which was taken as 1.0. The pGLB3 promoterless vector was used as a negative control, and the pRL-TK vector was used as internal control.

HCT-116 cells were plated in 6-well plates at 2×10$^5$ cells/well in McCoy's 5A media supplemented with 10% fetal bovine serum. After growth for 16 hr, plasmid mixtures containing 1 μg of NAG-1 promoter linked to luciferase and 0.1 μg of pRL-TK (Promega) were transfected by lipofectamine (Life Technologies) according to the manufacturer's protocol. After 24 hr, the media were changed to serum-free media and NSAIDs or TGZ were added. Cells were harvested in 1× luciferase lysis buffer after 24 hr of growth, and luciferase activity was determined and normalized to the pRL-TK luciferase activity using the Dual Luciferase Assay Kit (Promega).

The 3.5 kb NAG-1 promoter sequences were deposited in GenBank (accession number AF241308) and some restriction enzyme maps are shown in FIG. 5A. Several deletion clones were also generated by ExoIII nuclease from the 3.5 kb SmaI fragments. The deletion clones, pNAG2092, pNAG2021, pNAG1086, pNAG474, and pGL3 negative control vector, were transiently transfected into HCT-116 cells. As shown in FIG. 5B, the TGZ and/or INDO response elements are located between −1086 bp to −2021 bp of NAG-1 promoter. These data also suggest that INDO and TGZ might act by different mechanisms, since the TGZ showed greater induction of luciferase activity than INDO. Since several NSAIDs induce NAG-1 transcripts, the pNAG2021 clone containing the TGZ and/or INDO response element was used to determine if this region also responses to treatment with different NSAIDs. The treatment with TGZ or with various NSAIDs was found to induce reporter activity by 3-fold or 2- to 4-fold, respectively. FIG. 5C shows luciferase activity of 2021 bp NAG-1 promoter in the presence of TGZ or several NSAIDs. In these experiments, HCT-116 cells were transiently transfected with pNAG2021, treated with vehicle (0.2% DMSO), TGZ (10

μM), INDO (100 μM), aspirin (10 mM), ibuprofen (ibu, 1 mM), salicylate (SSA, 5 mM), sulindac sulfide (50 μM), sulindac (40 μM), or acetaminophen (acet, 100 μM) for 24 hr. The internal control vector (pRL-TK) was used to normalize the results to determine the transfection efficiency. The data presented here represent the mean±S.D. from 3 different experiments. Sulindac and acetaminophen did not increase luciferase activity (See, FIG. 5C). These data are consistent with the Northern data using NAG-1 as a probe (See, FIG. 2A). Interestingly, there is no obvious PPARγ response element (PPRE) with a direct repeat (DR-1) in this position, but there are 15 putative PPREs with a 4 bp mismatch in −1086 to −2021 position, suggesting that NAG-1 induction by NSAIDs and/or TGZ may be complex. However, the NAG-1 promoter between −1086 bp to −2021 bp does respond to the PPARγ ligands and/or NSAIDs.

EXAMPLE 7

Ectopic Expression of NAG-1 Induces Apoptosis

HCT-116 cells were stably transfected with an expression vector containing the full-length NAG-1 coding region in the sense and antisense orientations. The sense cells expressed NAG-1 protein at a level that was 2.0–2.5 fold greater than the vector transfected cells, while the anti-sense cells expressed slightly lower NAG-1 levels compared to vector transfected cells. FIG. 6A shows a Western analysis of ectopic expression of NAG-1 in HCT-116 cells. The full-length NAG-1 (sense strand and antisense strand) was cloned into the pCDNA3.1 expression vector and transfected into HCT-116 cells. Each cell was grown under G418 (500 μg/ml) for 2 weeks and treated with either vehicle or INDO (100 μM). After growing for 48 hr, the media was harvested, concentrated, and subjected to Western analysis. Thirty μg of total protein was loaded in each lane, and the arrow indicates the NAG-1 protein band.

Despite repeated attempts, construction of NAG-1 highly expressing cells which may be linked to high rates of apoptosis were not generated (data not shown). The sense-HCT-116 cells exhibited a slower growth rate compared to vector transfected cells or antisense-HCT-116 cells (data not shown). This could be due to effects on cell proliferation and/or an increase in cell death. A significant percentage of the sense-HCT-116 cells were found to undergo spontaneous apoptosis, as compared to the vector transfected HCT-116 cells. In contrast, the antisense-HCT-116 cells demonstrated lower spontaneous apoptosis at 48 hr (See, FIG. 6B). The stably transfected cells were then incubated with 100 μM indomethacin for 48 hr and the percentage of cells in apoptosis determined by FACS analysis as described in Example 1. The data shown in FIG. 6 represent mean±S.D. Indomethacin enhanced the percentage of apoptotic cells by approximately 2 fold in the vector-HCT-116 and sense cells.

In contrast, indomethacin did not stimulate apoptosis or increase the expression of NAG-1 in antisense HCT-116 cells. These results support the conclusion that NAG-1 expression is responsible, in part, for the INDO-induced apoptosis in HCT-116 cells.

EXAMPLE 8

NAG-1 Expression Reduces Transplantable Tumor Growth Rate

Since in vitro experiments showed that NAG-1 is strongly associated with apoptosis, anti-tumorigenic activity of NAG-1 in vivo was evaluated using NAG-1 stably transfected HCT-116 cells growing in athymic nude mice as follows. Twenty male nude mice (athymic NCr-nu) were purchased at 5 weeks of age from NCI/Taconic and maintained in pathogen-free conditions. Exponentially growing cells ($1 \times 10^6$ cells) vector and NAG-I transfected HCT-116 cells were inoculated subcutaneously behind the anterior forelimb into bilateral sides of each mouse. Ten mice were injected at two sites for each cell line. Tumors were measured externally on the indicated days in two dimensions using calipers. Tumor measurement began when the size was more than 3 mm in diameter (around 10 days after injection). Tumor volume was determined by the equation $V=(L \times W^2) \times 0.5$, where L=length and W=width of the tumor. Values are the mean (S.E. of 9 xenografts; See, FIG. 7B). "Vector" represents vector transfected HCT-116 cells, whereas "NAG-1" represents NAG-1 transfected HCT-116 cells. FIG. 7A provides a Western blot of transfected HCT-116 cells probed with anti-NAG-1 antibody.

As shown in FIG. 7C, the vector transfected HCT-116 cells rapidly developed visible tumors and dramatic growth was observed throughout the time course. In contrast, the NAG-1 transfected HCT-116 cells grew at a slower rate in the nude mice and suppressed tumor growth. Thus, data from in vitro and in vivo studies, indicate that NAG-1 has anti-tumorigenic activity which may be mediated by an increase in apoptosis.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art of molecular biology, oncology, and/or related fields are intended to be within the scope of the following claims.

We claim:

1. An isolated or purified nucleic acid comprising a nucleic acid sequence comprising SEQ ID NO:3 and a heterologous nucleic acid reporter construct wherein the nucleic acid sequence comprising SEQ ID NO:3 directs transcription of the heterologous reporter construct.

2. A composition comprising the isolated or purified nucleic acid of claim 1.

3. An expression vector comprising the isolated or purified nucleic acid of claim 1.

4. A method of screening a compound for antagonistic or agonistic activation of a NAG-1 promoter region comprising a nucleic acid sequence comprising SEQ ID NO:3 comprising the steps of:
   a) providing in any order;
      i) cells comprising a recombinant expression vector, wherein said vector comprises the nucleic acid sequence comprising SEQ ID NO:3 and at least one heterologous nucleic acid reporter construct, wherein the nucleic acid sequence comprising SEQ ID NO:3 directs transcription of the heterologous reporter construct; and,
      ii) at least one compound;
   b) contacting cells with said compound to produce treated cells under conditions such that said reporter construct is expressed;
   c) detecting the expression of said reporter construct in said treated cells; and
   d) comparing said expression of the reporter construct in said treated cells to expression of a reporter construct in control cells.

5. The isolated or purified nucleic acid of claim 1, wherein the nucleic acid sequence comprises SEQ ID NO: 1.

6. An isolated or purified nucleic acid consisting of SEQ ID NO: 3 and SEQ ID NO: 2.

7. An isolated or purified nucleic acid consisting of SEQ ID NO: 1 and SEQ ID NO: 2.

8. The method of claim 4, wherein the recombinant expression vector comprises SEQ ID NO:1.

* * * * *

SEQUENCE LISTING

<160> NUMBER OF SEQ ID NOS: 5

<210> SEQ ID NO 1
<211> LENGTH: 8902
<212> TYPE: DNA
<213> ORGANISM: Homo sapiens

<400> SEQUENCE: 1

-continued

```
gaattcgagc tcggtacccg ggatcgatc  ctctagagtc gacctgcagg catgcaagct    60
tgcggccgcc ctaggactag tctcgaggct agcccatggg gcgccgggcc cggatcacct   120
gaggtccgga gttcgagatc agcctgggca acacggtgaa accccgtct  ctactaaaaa   180
ttcaaaaatt agctgggcat ggtggtgcat gcctgtaatc ccagctactc gggaggctaa   240
ggcaggagaa tcgtttgaac ccaggaggtg gagactgcag tgagtcgaga tggcgccatt   300
gcactccagc ctgggcaaca agagtaaatc tccatctcac aaaaaaaaaa aaaaaaagca   360
aggcacagtg gcatcaggct ggggtgggaa gatcacttga gcccagccat tcgagaccaa   420
cctgtgcaac acaggaaaac cccattctac aaaatagtaa aaaattatca gggcatggtg   480
gcacatgcct atagtcccag ctactcggga gagtgatggg ggaggatcac ttgagcccag   540
gaggtcgagg ctgcggtgac ctatgattgt gccactgcac tccagcctgg gctacacagc   600
cagaccctgt ctaaaagaa  acaaaacagg caggacgcgg tggctcacac ctgtaatccc   660
agcactttgg gaggccgagg tgggcggatc acctgacatc aggagttcga gaccagcctg   720
tccaacatcg tgaaatcccc ctctctacta aaatacaaac attaaccggg catggtagtg   780
ggtgcctgta atcctaccta ctcgggaggc tgaggcagga aaattgcttg aacctgggag   840
atggaggttg caatgagccg agatcgcgcc actgcacgac agcctaggcg acagaacaag   900
actccatctc aaaaaaaaa  gaaaagaaa  aaaagaagaa actctcattg atgggtgttc   960
attgatggag cacttttttg gaatgggttg acatgctcac agtgttttta acctcacctc  1020
gtctctgaag aggtgcagat aaaagtcacc tggtgaggaa aatgccttt  taaaaacaat  1080
ttttagaggg ccagcacggt gactcacgac tgtaatctga gcaatttggg aggccgaggt  1140
gggcggatca cttgaggtca ggagttcaaa accagtctgg ccaacatggt gaaatcctgt  1200
ctctactaaa aatacaaaaa ttagttgggc atggtggcac atgcctgtaa tcccagctac  1260
tcgggaagct gaggcaggag aatcacttta acccaggagg tggaagttgc agtgagccaa  1320
gatcgcgcca gtgcactcca gcctgggcaa cagagcgaga ctctgtctca aagaaaaaa   1380
aaaagagatg gggtcttggg gtctcactgt gttgcccagg ctggtctcca actcctggcc  1440
tcaagcaatc ctcctgcttt ggcctcccaa agtgctagga ttacatgcct gagccactgt  1500
gttcaaccag ggtgtcccctt ttctgagact gcattcttcc caccttgccc aagtattgca  1560
ggagaaacac aagccccatg ctgtgctggc gaaatctcat ctcatgctgg cctgttaggg  1620
tggccatatc ctctcatttc aagaggctct gagggagatg gaacaggctc agcggctggc  1680
tgcttggggc tctaaccccca gccctgctgt cttctggctg tgtggccgtg acgagcccac  1740
ctctctggcc tcagtttgtc atctgtgaaa tggacataat ctatccacca catcaggctg  1800
tataaagatt aggccaggtg tggtgcctca cacctgtaat cccagcgctt tgggaggctg  1860
aggcaggcag atcacctaag gtcaggagtt cgagaccaac ctggccaaaa tggtgaaacc  1920
ctgtctctaa taaaaataca aaaattagct gggcatggtg gcatgtacct gtaatcccag  1980
ctacccagga ggctgaggca ggagaatcgc tggaacccgg gaggcagagg ctgcagtgag  2040
ccaagattgc accactgcac tccagcctga gtgacagagc gaaactccgt ctcagagaaa  2100
aaaaaaaaa  aaaagatat  gtccaactcc taacgctcag tatctgtgac cttatttgga  2160
aagaaggtct ttgcaaatgt aattaaacta agatcttgt  actgagatca ttctgaatta  2220
aaaatggacc cgtggctggg cacagtggct cacacctgta atcccagcac tctgggaggc  2280
tgaggtgggc aaatcacctg aaatcaggag ttcaaaacca gcctggccaa catggcgaaa  2340
```

-continued

```
ccccgtctct actaaaaata caaaaaaaaa ttagctgggc gttgtggtgc acacctgtaa    2400
ttccagctac tcgggaggct gaggcaggag aatcacttga acctgggagg ctgcagtgag    2460
ccgagattgc gccactgcat tccagcctag gcaacaagag tgaaactctg tctcgaaaat    2520
aaaaacataa gaaagagtgg acccatggcc aggcacagtg gctcatgcct ataatcccaa    2580
cactttggga ggccaagatg gaaagatcgt ttgaactcag ccgtttgaaa ccagcctggg    2640
caacatagtg agaccctgtg tctaaataca aacacaaaca gaaaacaaaa agaacccggg    2700
ctggctgcgg aaccccctag atggcacagg cacatccggg cttcgaggac agtcacgag    2760 catgagacag catttcttct tgtcctcggg gcctgcagga agttttaag taatctgctt    2820 ttgtgcctct tccaaatctc ctcctatgac cctgtttacc ttacatcaca agaaacaatc    2880
aataaaagtg gtttgtgttc gtgagtgccg tgtgtttgac aaaggcgttg ataactgaga    2940
gctggtagtg gaggggggag attttgggag attggggccc tgccaggtgg acggactggc    3000
ctgacctccg gcccctgcgc tctgtttact tccatcccag ctccacctct ggggacccat    3060
ggaagctgtc ggtgaggaac acaggatccg acctgctgag ctcatctctg gccacctgcc    3120
tgcatccgcc ccatctctcc tctcagcttg gccatgaggc gggctatgag gtcattggtt    3180
aaagatttgg ggaagcagag ccaggcgagt ggccagatgt ggtggctcat gccatcacag    3240
gatccagcac tgtgagagga caaggaagga ggatccttga cctcaggagt tcaaaaccag    3300
cctgtacaac atagcaagac ccccgtctct acaaaatata aaattaacca gttgtggagg    3360
cacgcgcctc tattcccaac tactcgggag gttgaggtga caggatccct tgacccagga    3420
ggtcgaggct gcattgagtg ggtaacagag ccaaaccctg tctctaaaac aaacaaaaca    3480
gaaacaaaaa gtacactact tactgtcctg cttctcacca ttccagcctg ggtagtcctt    3540
tttttttttt ttgagacagg gtcttgctca ttgctcaggc tggagtgcag aagcgtaatc    3600
acagctcact gcagccttga tctccaaaaa gactaccagc ttggctgggt gtggggactc    3660
atgcctataa ccccagcatt tgggagccca gaggcaagag gattccttga gccaaggagt    3720
tcgagaccag cctgggcaac acagtgagac cctatctcta aaatttttt ttttgagatg    3780 gaatttagct ctcattgccc aggctagagt gcaatggtgc aatctcagct caccacaatc    3840
tccacctccc aggttcaagc aaaattctcc tgcctcagcc tcccgagtag ctgggattac    3900
aggcatgcgc caccatgccc ggctaatttt gttttttaaa gacgggggt tctccatgtt    3960 ggtcaggctg gtctcaaact cccaacctca ggtgatctgc ctgccttggc ctccctatct    4020
cctcattggg ggccatagga ttaaatagct ttttctttt tttatgagac ggagtttctc    4080
tgtgtcccac aggttggagg cagtggcaca atcacggctc acggcaacct ccgcctcctg    4140
cctcagccta ctgagtagct gggattacag tcatgcgcca ccacatctgg ccatcttgtg    4200
tgtttgagta atctcggtat atatccattt tgtctatgaa gctcgttaat ttgggcccca    4260
aagcacccgc tggcaatggc ctttaagtgc gaaaatcctg gcattaggcg tcccccacct    4320
tttttttttt tttttgttgg gacggatgta ggtgtgtcgc ccaggctgga gtgcagtggc    4380
gcaatctcgg ctcactgcaa gctccgcctt ccgggttcac gcctttctcc cacctcagcc    4440
tcccgagtag ctgagactac aggcacccac caccatgcct ggctaatttt tttgtatttt    4500
tagtagagag ggggtttcac cgtgttagcc aggatggtct tgatctcctg acctcgtgat    4560
ccgcctgacc tcggccttcc aaagtgctgg gattacaggc aagagccacc gcgcccggcc    4620
tggtgtcctt atttcttggg aaaggataca gagggtcaga gaggcgcccc agcttgtgca    4680
ggaatgcatt cctgagatct ggcctggccg tggtcactgg agtgtttact ctgcttacag    4740
```

-continued

```
ggtctggtgt agtgggggat ggctgggtag gaacgtgcgg gctataaagc cagaccccag    4800
gtgtcagtgc ggttcagaaa gcaactagca cagccatgcc caggccagga cccgtgacac    4860
agcgatgctc tcagatgctg ctgatgttac agatgttgtt gggggcaccc tgactctgca    4920
ggtgagacct tctgggttcc taggacccct ggacaagcac tttgatccgg atgactccag    4980
gtcccaggag ttgcagaaac gccaccagga ctttcagagc cccagttaga caaggagagc    5040
ccaggaggag ttggcccccca ccctcatccc aaaagcacag gtgagctttg agacctccca    5100
cccccaggac agcccccatg tctatttttct ttttctttaa agatgttctt atttgggggc    5160
ccaggcgtgg tggctcatgc ctgtaatccc agcactttgg gaggccgagg caggcggatc    5220
acctgagatc aggagttcga gaccagactg gccaacatga cagggtgaga ccccatcttt    5280
acaacaaata caaaaattac ccaggcatgg tggcacacgc ctgtaatccc agctactagg    5340
gaggatgaag caggagaatt gcttgaaccc gggaggcgga gattgtagtg agttgagatc    5400
gcacaactgc actccagcct gggcaacaga gggagactcc aatccaaaaa aagaaaaaa    5460 atccccctagg acagggctgt ggctgagacc ctgagggctg gaggcttggc tggccttgca    5520
cagcagcggg tgcatgctgg ggtggggaga ggcctggaga ccctgtgact ccactggggg    5580
ccttgctgtg tgaccccta gtgagtcctt gtgtctctta cccacgcatg cctgtcacat    5640
gcagacaccc acacacaccc agtatctgcc ggacagggca gcccttcctc tccgcagcca    5700
ggaagctgga cataggcaca agggctgacg cctggggcca ggaatcctgc ctgagcatta    5760
ggataaggtc tgggaacccc aggggaaagg gcactcctgg ggcatcccct gcccctctac    5820
catctggtgg gcttggactc ttacaccaag cctgccctgc tctaaaaccc cactctcaat    5880
tctgtgccac ctcctctctg ggcccagaca agagcagatt catccctgcc ccaaaggaac    5940
caccagtctt gggtcagcag agctgggcac agacacttcc agtgccgtgg ggctgtaact    6000
gtgataggtc tgttgctcca tgcacttggc aagtcaacag ctgagaaaac aggttgcaac    6060
atggaaagag ttttaatccg accggcgtgg tggctcatgc ctgtaatccc agcactttgg    6120
gaggctgagg cgggtggatc atctgaggcc agcagttcaa gatcagcctg ccaaccagg    6180 tgaaacctca tctctactaa aaatacaaaa attagccagg cgtgatggtg cgcacctgta    6240
atcccagcta cttgggaggc tgaggcagga gaatcaattg aacctgggag gcggaggttg    6300
cagtgagcca agatcatacc actgcactcc agcctgggca acagagcgag agactgtctc    6360
ggaagaaaaa aaaaaaaaaa aggctggggg cagtggctca tgcctgtaat ccccacactt    6420
taaaggcaga ggccgacgga tgacttgagg tcaagagttc gagacctgcc tggcaacatg    6480
gtgaatcacc gtctctacta aaacacaaa attagccagg tgtggtggcg catgactgta    6540
atcccagcta ctcagtaggc tgaggcagga ggcggaggtt gcagtgagcc gagattgtgc    6600
cactgcactc caacctgggg gacagagaga actccgtct caaaaaaaaa aaaaaaaga    6660 gatttaatcc tagggccacc caatgaggag ataggaggga acctcaaatc catttccagg    6720
aggaggagtt tggggccata taaatgtata tatacaaata tatatatatt tttaagatgg    6780
agtcagccgg ccgtggtggc tcacgcctct aatcccaata ctttgggagg ccgaggccgg    6840
cggatcacaa ggtcaggaga ttgagaccat cttagctaac acggtgaaac cccatctcta    6900
ctaaaaatac aaaaaaaaat tagccaggcg tggtgggggg tgatcatagt cccagctact    6960
caggaggttg aggcaggaga atagcatgaa cctgggagct ggagcttgca ggttggagtg    7020
caatggcatg atctcagctc aatgcacctc cgcctcctgg ttcagcgatt tctcctgcct    7080
```

```
caggctcccg agcagctggg attacaggca tgtgcccacc acgaccggtt aatttctgaa    7140
ttttttagta gagacaggtt tcatcatgtt gtcaggctgg tctcgaactc ctgacctcag    7200
gtgatccgcc cgccttggcc tcccaaagtg ctgggattac aggcgtgagc cactgcacct    7260 ggccagggc tagagtttta attttaagg attttggagt gggctgaagt gtggaggtca      7320
ttgcttggtg aaagagtgca ggaggtgaag tcacagacag taagaaactg tattctcatg    7380
cagattccgt tcctctgtgg ggtcttcaca ctggtgggtg tcattggtta aggatttcaa    7440
aaacatctta agaaattctt ctaaaaagtc ttatgattct aaggtcggaa atcacatcta    7500
tagcaaatgg tcggtatcag gtgctacaag caacttgcgg tcacaaggaa gtgggtcaaa    7560
gtgcagcctg attagtgctt aattataact aagtttctgt ccagaattct ttttttttga    7620
gacagagttt tgctcttgtt gatcaggcgg aagtgcaatg gtgaaaactt ggctcactgc    7680
aacctccgcc ctctgggttc aagcgattct cttgcttcag cctctcgaat agctgggatt    7740
acaggcatgt aatcccacca ccaagcccag ctaattttgt atatttagta gagacagggt    7800
ttctccatgt tggtcaggct agtctagaac tcttgacgtc agatgatcca cgtgcctcgg    7860
cctcccaaag tgctgggatt acaggcgaga gccaccgtgc ccggcgcaga attctttttt    7920
ttagagatga ggtattgcca tcttgcccag acttgtctcg aactcctggg ctcaaacaat    7980
ccacccacct cggcctccca aagtgctgag attactgaca taagccacca tgcctggccc    8040
ccagaattat gaatcctgtg aggatggctt caaggtgagc gctgagccag acaaaaggat    8100 gggtttggg agcaccctgc ttagactgga aagataatgt tggagaagac ttcctggaag    8160
aggggctttt tgcgtagagt tttgaagaat gagtaggagt tctccagagg aggatgagta    8220
actgcaataa cacccagttt atcaagtgcc tcctatgtgt ctggccctgt gctttacccc    8280
tcatttgacc acctctccag tgagagtctc agtcctttt ttcctggtga ggaaacaggc     8340
atggcagaga ggcatgacac atcaaggttg cccttcctgg ctccatctag cccgttctcc    8400
tctgcttcct ttgttttttca ccatctttag cctttgaccc caaccaaaaa gagaagagag    8460
gaaatcccat gggcatagac agccacctct taaactcttg tctggaattt ttcacatagt    8520
aacaatgtct ttttttcctc caaaaagact cccaggctgg aatggtgtcc tcatatcgag    8580
gaagaggata ctgaggccca gaaatgtgcc ctagctttac taggagcgcc cccacctaaa    8640
gatcctcccc ctaaatacac ccccagaccc cgcccagctg tggtcattgg agtgtttact    8700
ctgcaggcag ggggaggagg gcgggactga gcaggcggag akggacaaag tccggggact    8760
ataaaggccg gtccggcagc atctggtcag tcccagctca gagccgcaac ctgcacagcc    8820
atgcccgggc aagaactcag gacggtgaat ggctctcaga tgctcctggt gttgctggtg    8880
ctctcgtggc tgccgcatgg gg                                             8902
```

<210> SEQ ID NO 2
<211> LENGTH: 1202
<212> TYPE: DNA
<213> ORGANISM: Homo sapiens

<400> SEQUENCE: 2

```
gcggccgctg cacagccatg cccgggcaag aactcaggac gctgaatggc tctcagatgc      60
tcctggtgtt gctggtgctc tcgtggctgc cgcatggggg cgccctgtct ctggccgagg     120
cgagccgcgc aagtttcccg ggaccctcag agttgcacac cgaagactcc agattccgag     180
agttgcggaa acgctacgag gacctgctaa ccaggctgcg ggccaaccag agctgggaag     240
attcgaacac cgacctcgtc ccggccctg cagtccggat actcacgcca gaagtgcggc      300
```

```
tgggatccgg cggccacctg cacctgcgta tctctcgggc cgcccttccc gagggctcc     360 ccgaggcctc ccgccttcac cgggctctgt tccggctgtc cccgacggcg tcaaggtcgt    420
gggacgtgac acgacctctg cggcgtcagc tcagccttgc aagacccag gcgcccgcgc     480 tgcacctgcg actgtcgccg ccgccgtcgc agtcggacca actgctggca gaatcttcgt    540
ccgcacggcc ccagctggag ttgcacttgc ggccgcaagc cgccagggg cgccgcagag     600 cgcgtgcgcg caacggggac cactgtccgc tcgggcccgg gcgttgctgc cgtctgcaca    660
cggtccgcgc gtcgctggaa gacctgggct gggccgattg ggtgctgtcg ccacgggagg    720
tgcaagtgac catgtgcatc ggcgcgtgcc cgagccagtt ccgggcggca acatgcacg     780 cgcagatcaa gacgagcctg caccgcctga agcccgacac ggtgccagcg ccctgctgcg    840
tgcccgccag ctacaatccc atggtgctca ttcaaaagac cgacaccggg gtgtcgctcc    900
agacctatga tgacttgtta gccaaagact gccactgcat atgagcagtc ctggtccttc    960
cactgtgcac ctgcgcgggg gaggcgacct cagttgtcct gccctgtgga atgggctcaa    1020
ggttcctgag acacccgatt cctgcccaaa cagctgtatt tatataagtc tgttatttat    1080
tattaattta ttggggtgac cttcttgggg actcggggc tggtctgatg gaactgtgta     1140
tttatttaaa actctggtga taaaaataaa gctgtctgaa ctgttaaaaa aaaaaaaaa     1200 aa                                                                   1202
```

<210> SEQ ID NO 3
<211> LENGTH: 3535
<212> TYPE: DNA
<213> ORGANISM: Homo sapiens
<220> FEATURE:
<221> NAME/KEY: misc_feature
<222> LOCATION: (65)..(65)
<223> OTHER INFORMATION: "n" = any nucleic acid
<220> FEATURE:
<221> NAME/KEY: misc_feature
<222> LOCATION: (1058)..(1058)
<223> OTHER INFORMATION: "n" = any nucleic acid
<220> FEATURE:
<221> NAME/KEY: misc_feature
<222> LOCATION: (1064)..(1064)
<223> OTHER INFORMATION: "n" = any nucleic acid
<220> FEATURE:
<221> NAME/KEY: misc_feature
<222> LOCATION: (1071)..(1071)
<223> OTHER INFORMATION: "n" = any nucleic acid

<400> SEQUENCE: 3

```
cccgggaggc ggagattgta gtgagttgag atcgcacaac tgcactccag cctgggcaac    60
agagngagac tccaatccaa aaaaagaaa aaatcccct aggacagggc tgtggctgag      120
accctgaggg ctggaggctt ggctggcctt gcacagcagc gggtgcatgc tggggtgggg    180
agaggcctgg agaccctgtg actccactgg gggccttgct gtgtgacccc ctagtgagtc    240
cttgtgtctc ttacccacgc atgcctgtca catgcagaca cccacacaca cccagtatct    300
gccggacagg gcagcccttc ctctccgcag ccaggaagct ggacataggc acaagggctg    360
acgcctgggg ccaggaatcc tgcctgagca ttaggataag gtctgggaac cccaggggga    420
agggcactcc tggggcatcc cctgcccctc taccatctgg tgggcttgga ctcttacacc    480
aagcctgccc tgctctaaaa ccccactctc aattctgtgc cacctcctct ctgggcccag    540
acaagagcag attcatccct gccccaaagg aaccaccagt cttgggtcag cagagctggg    600
cacagacact tccagtgccg tggggctgta actgtgatag gtctgttgct ccatgcactt    660
```

-continued

| | |
|---|---|
| ggcaagtcaa cagctgagaa aacaggttgc aacatggaaa gagttttaat ccgaccggcg | 720 |
| tggtggctca tgcctgtaat cccagcactt tgggaggctg aggcgggtgg atcatctgag | 780 |
| gccagcagtt caagatcagc ctggccaacc aggtgaaacc tcatctctac taaaaataca | 840 |
| aaaattagcc aggcgtgatg gtgcgcacct gtaatcccag ctacttggga ggctgaggca | 900 |
| ggagaatcaa ttgaacctgg gaggcggagg ttgcagtgag ccaagatcat accactgcac | 960 |
| tccagcctgg gcaacagagc gagagactgt ctcggaagaa aaaaaaaaa aaaaggctgg | 1020 |
| gggcagtggc tcatgcctgt aatccccaca ctttaaangc agangccgac ngatgacttg | 1080 |
| aggtcaagag ttcgagacct gcctggcaac atggtgaatc accgtctcta ctaaaaacac | 1140 |
| aaaattagcc aggtgtggtg gcgcatgact gtaatcccag ctactcagta ggctgaggca | 1200 |
| ggaggcggag gttgcagtga gccgagattg tgccactgca ctccaacctg ggggacagag | 1260 |
| agaaactccg tctcaaaaaa aaaaaaaaa agagatttaa tcctagggcc acccaatgag | 1320 |
| gagataggag ggaacctcaa atccatttcc aggaggagga gtttgggggcc atataaatgt | 1380 |
| atatatacaa atatatatat attttttaaga tggagtcagc cggccgtggt ggctcacgcc | 1440 |
| tctaatccca atactttggg aggccgaggc cggcggatca aaggtcagg agattgagac | 1500 |
| catcttagct aacacggtga aaccccatct ctactaaaaa tacaaaaaaa aattagccag | 1560 |
| gcgtggtggg gggtgatcat agtcccagct actcaggagg ttgaggcagg agaatagcat | 1620 |
| gaacctggga gctggagctt gcaggttgga gtgcaatggc dtgatctcag ctcaatgcac | 1680 |
| ctccgcctcc tggttcagcg atttctcctg cctcaggctc ccgagcagct gggattacag | 1740 |
| gcatgtgccc accacgaccg gttaatttct gaattttta gtagagacag gtttcatcat | 1800 |
| gttgtcaggc tggtctcgaa ctcctgacct caggtgatcc gccgcccttg gcctcccaaa | 1860 |
| gtgctgggat tacaggcgtg agccactgca cctggccagg gctagagtt ttaattttta | 1920 |
| aggattttgg agtgggctga agtgtggagg tcattgcttg gtgaaagagt gcaggaggtg | 1980 |
| aagtcacaga cagtaagaaa ctgtattctc atgcagattc cgttcctctg tggggtcttc | 2040 |
| acactggtgg gtgtcattgg ttaaggattt caaaaacatc ttaagaaatt cttctaaaaa | 2100 |
| gtcttatgat tctaaggtcg gaaatcacat ctatagcaaa tggtcggtat caggtgctac | 2160 |
| aagcaacttg cggtcacaag gaagtgggtc aaagtcagc ctgattagtg cttaattata | 2220 |
| actaagtttc tgtccagaat tcttttttt tgagacagag ttttgctctt gttgatcagg | 2280 |
| cggaagtgca atggtgaaaa cttggctcac tgcaacctcc gccctctggg ttcaagcgat | 2340 |
| tctcttgctt cagcctctcg aatagctggg attacaggca tgtaatccca ccaccaagcc | 2400 |
| cagctaattt tgtatattta gtagagacag ggtttctcca tgttggtcag gctagtctag | 2460 |
| aactcttgac gtcagatgat ccacgtgcct cggcctccca agtgctggg attacaggcg | 2520 |
| agagccaccg tgcccggcgc agaattcttt tttttagaga tgaggtattg ccatcttgcc | 2580 |
| cagacttgtc tcgaactcct gggctcaaac aatccaccca cctcggcctc ccaaagtgct | 2640 |
| gagattactg acataagcca ccatgcctgg ccccagaat tatgaatcct gtgaggatgg | 2700 |
| cttcaaggtg agcgctgagc cagacaaaag gatgggttt gggagcaccc tgcttagact | 2760 |
| ggaaagataa tgttggagaa gacttcctgg aagaggggct ttttgcgtag agttttgaag | 2820 |
| aatgagtagg agttctccag aggaggatga gtaactgcaa taacacccag tttatcaagt | 2880 |
| gcctcctatg tgtctggccc tgtgctttac ccctcatttg accacctctc cagtgagagt | 2940 |
| ctcagtccct ttttttcctgg tgaggaaaca ggcatggcag agaggcatga cacatcaagg | 3000 |
| ttgcccttcc tggctccatc tagcccgttc tcctctgctt cctttgtttt tcaccatctt | 3060 |

```
tagcctttga ccccaaccaa aaagagaaga gaggaaatcc catgggcata gacagccacc    3120
tcttaaactc ttgtctggaa tttttcacat agtaacaatg tctttttttc ctccaaaaag    3180
actcccaggc tggaatggtg tcctcatatc gaggaagagg atactgaggc ccagaaatgt    3240
gccctagctt tactaggagc gcccccacct aaagatcctc ccctaaata caccccaga     3300 ccccgcccag ctgtggtcat tggagtgttt actctgcagg caggggggagg agggcgggac   3360 tgagcaggcg gagacggaca aagtccgggg actataaagg ccggtccggc agcatctggt   3420
cagtcccagc tcagagccgc aacctgcaca gccatgcccg ggcaagaact caggacggtg   3480
aatggctctc agatgctcct ggtgttgctg gtgctctcgt ggctgccgca tgggg         3535

<210> SEQ ID NO 4
<211> LENGTH: 23
<212> TYPE: DNA
<213> ORGANISM: Homo sapiens

<400> SEQUENCE: 4
acctgcacag ccatgcccgg gca                                              23

<210> SEQ ID NO 5
<211> LENGTH: 23
<212> TYPE: DNA
<213> ORGANISM: Homo sapiens

<400> SEQUENCE: 5
cagtggaagg accaggactg ctc                                              23
```